US010746748B2

(12) United States Patent
Yabutani et al.

(10) Patent No.: US 10,746,748 B2
(45) Date of Patent: Aug. 18, 2020

(54) AUTOMATIC ANALYSIS DEVICE AND AUTOMATIC ANALYSIS METHOD

(71) Applicant: Hitachi High-Technologies Corporation, Tokyo (JP)

(72) Inventors: Chie Yabutani, Tokyo (JP); Naoto Suzuki, Tokyo (JP); Akihisa Makino, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 458 days.

(21) Appl. No.: 15/554,276

(22) PCT Filed: Feb. 12, 2016

(86) PCT No.: PCT/JP2016/054058
§ 371 (c)(1),
(2) Date: Aug. 29, 2017

(87) PCT Pub. No.: WO2016/152305
PCT Pub. Date: Sep. 29, 2016

(65) Prior Publication Data
US 2018/0080948 A1     Mar. 22, 2018

(30) Foreign Application Priority Data
Mar. 20, 2015   (JP) ................................. 2015-057503

(51) Int. Cl.
*G01N 33/86*     (2006.01)
*G01N 35/10*     (2006.01)
(Continued)

(52) U.S. Cl.
CPC ........... *G01N 33/86* (2013.01); *G01N 21/272* (2013.01); *G01N 21/82* (2013.01);
(Continued)

(58) Field of Classification Search
None
See application file for complete search history.

(56) References Cited

U.S. PATENT DOCUMENTS 8,278,108 B2    10/2012   Wada et al.
8,460,935 B2     6/2013   Kurono et al.
(Continued)

FOREIGN PATENT DOCUMENTS

CN   102066947 A   5/2011
CN   104350386 A   2/2015
(Continued)

OTHER PUBLICATIONS

Japanese Office Action received in corresponding Japanese Application No. 2017-507588 dated Aug. 21, 2018.
(Continued)

*Primary Examiner* — Benjamin R Whatley
(74) *Attorney, Agent, or Firm* — Mattingly & Malur, PC

(57) ABSTRACT

The automatic analysis device 100 is provided with: a specimen dispensing mechanism 101 that dispenses subject blood plasma and/or normal blood plasma to be added to correct the coagulation time of the subject blood plasma, into a plurality of specimen containers 103; reaction containers 104 that contain the subject blood plasma and/or the normal blood plasma; a reagent dispensing mechanism 106 that dispenses a reagent into the reaction containers 104; and a detecting unit 113 which applies light from a light source 115 to the subject blood plasma and/or the normal blood plasma to which the reagent is added in the reaction containers 104, and which measures the coagulation time on the basis of the obtained scattered light and/or transmitted light.

20 Claims, 19 Drawing Sheets

(51) Int. Cl.
*G01N 35/02* (2006.01)
*G01N 35/04* (2006.01)
*G01N 33/96* (2006.01)
*G01N 21/82* (2006.01)
*G01N 33/49* (2006.01)
*G01N 35/00* (2006.01)
*G01N 21/27* (2006.01)
*G01N 1/38* (2006.01)

(52) U.S. Cl.
CPC ......... *G01N 33/4905* (2013.01); *G01N 33/96* (2013.01); *G01N 35/00* (2013.01); *G01N 35/0092* (2013.01); *G01N 35/0095* (2013.01); *G01N 35/00722* (2013.01); *G01N 35/00732* (2013.01); *G01N 35/02* (2013.01); *G01N 35/025* (2013.01); *G01N 35/04* (2013.01); *G01N 35/1002* (2013.01); *G01N 1/38* (2013.01); *G01N 2035/0094* (2013.01); *G01N 2035/00356* (2013.01); *G01N 2035/00534* (2013.01); *G01N 2035/00544* (2013.01); *G01N 2035/00554* (2013.01); *G01N 2035/00831* (2013.01); *G01N 2035/00891* (2013.01); *G01N 2035/0441* (2013.01); *G01N 2035/0444* (2013.01)

(56) References Cited

U.S. PATENT DOCUMENTS

| | | | |
|---|---|---|---|
| 2010/0210019 A1* | 8/2010 | Kurono | G01N 35/00613 436/8 |
| 2011/0129862 A1* | 6/2011 | Nakamura | G01N 33/86 435/13 |
| 2014/0065018 A1 | 3/2014 | Imazu et al. | |
| 2014/0087472 A1* | 3/2014 | Kurono | G01N 35/00613 436/47 |
| 2014/0170023 A1* | 6/2014 | Saito | G01N 35/0095 422/65 |
| 2014/0295470 A1 | 10/2014 | Okuda et al. | |
| 2015/0104351 A1* | 4/2015 | Makino | G01N 35/1004 422/64 |
| 2015/0111235 A1 | 4/2015 | Nakamura et al. | |
| 2020/0064365 A1 | 2/2020 | Makino et al. | |

FOREIGN PATENT DOCUMENTS

| | | |
|---|---|---|
| CN | 103688177 A | 5/2019 |
| JP | 63-005268 A | 1/1988 |
| JP | 5-164761 A | 6/1993 |
| JP | 8-101216 A | 4/1996 |
| JP | 2001-249137 A | 9/2001 |
| JP | 2008-185597 A | 8/2008 |
| JP | 2009-8552 A | 1/2009 |
| JP | 2009-204446 A | 9/2009 |
| JP | 2010-190641 A | 9/2010 |
| JP | 20149972 A | 1/2014 |
| JP | 2014-052391 A | 3/2014 |
| JP | 201448112 A | 3/2014 |
| JP | 2014-190954 A | 10/2014 |
| JP | 2015-031586 A | 2/2015 |
| WO | 2009/153964 A1 | 12/2009 |
| WO | 2013/035418 A1 | 3/2013 |
| WO | WO-2013035418 A1 * | 3/2013 ........... G01N 35/026 |
| WO | 2013/187210 A1 | 12/2013 |
| WO | WO-2013187210 A1 * | 12/2013 ....... G01N 35/00584 |
| WO | 2014203663 A1 | 12/2014 |
| WO | 2012/173250 A1 | 2/2015 |

OTHER PUBLICATIONS

Automated Coagulation Analyzer CP3000, Instrument for blood test, Coagulation analyzer, General medical device (class I), Specifically-maintained medical device, May 12, 2014 (May 12, 2014), pp. 1 to 3.
Mitsuko Yamato et al., "Basic performance of fully-automated coagulation analyzer CP3000 and comparison with CP2000", Japanese Journal of Clinical Laboratory Automation, 2014, vol. 39, No. 4, pp. 539.
"Special feature: Current situation of automated analyzer for clotting test", Features and availability of fully-automated coagulation analyzer "CAPRESTA 2000", Biological Sample Analysis vol. 32, No. 5 (2009) pp. 386 to 392.
International Search Report of PCT/JP2016/054058 dated Apr. 5, 2016.
Chinese Office Action received in corresponding Chinese Application No. 201680016754.3 dated May 15, 2019.
Japanese Office Action received in corresponding Japanese Application No. 2017-507588 dated Jul. 12, 2018.
Japanese Office Action received in corresponding Japanese Application No. 2017-507588 dated Jul. 17, 2018.
The Saitama Journal of Medical Technology (Sairingikaisi), 2009, pp. 258 to 259. vol. 56, No. 2.
"COAPRESTA 2000" Apr. 2008 with partial translation.
Sixth Edition of Instruction Manual of COAPRESTA 2000, Instruction Manual Version 2.02, Sekisui Medical Co., Ltd., Sep. 1, 2012.
Yoshiko Tamai, et al., III. Diagnosis and Treatment, 5. Acquired Hemophilia, Nihon Naika Gakkai Zasshi, Jul. 10, 2014, vol. 103, No. 7, p. 1622 to 1630.
Extended European Search Report received in corresponding European Application No. 16768208.7 dated Oct. 29, 2018.
Kagawa, K. "Blood Coagulation Compensation Test", Dec. 31, 2006, pp. 735-742, vol. 34, No. 8.
Japanese Office Action received in corresponding Japanese Application No. 2019-138425 dated Jun. 30, 2020.

* cited by examiner

[Fig. 1]
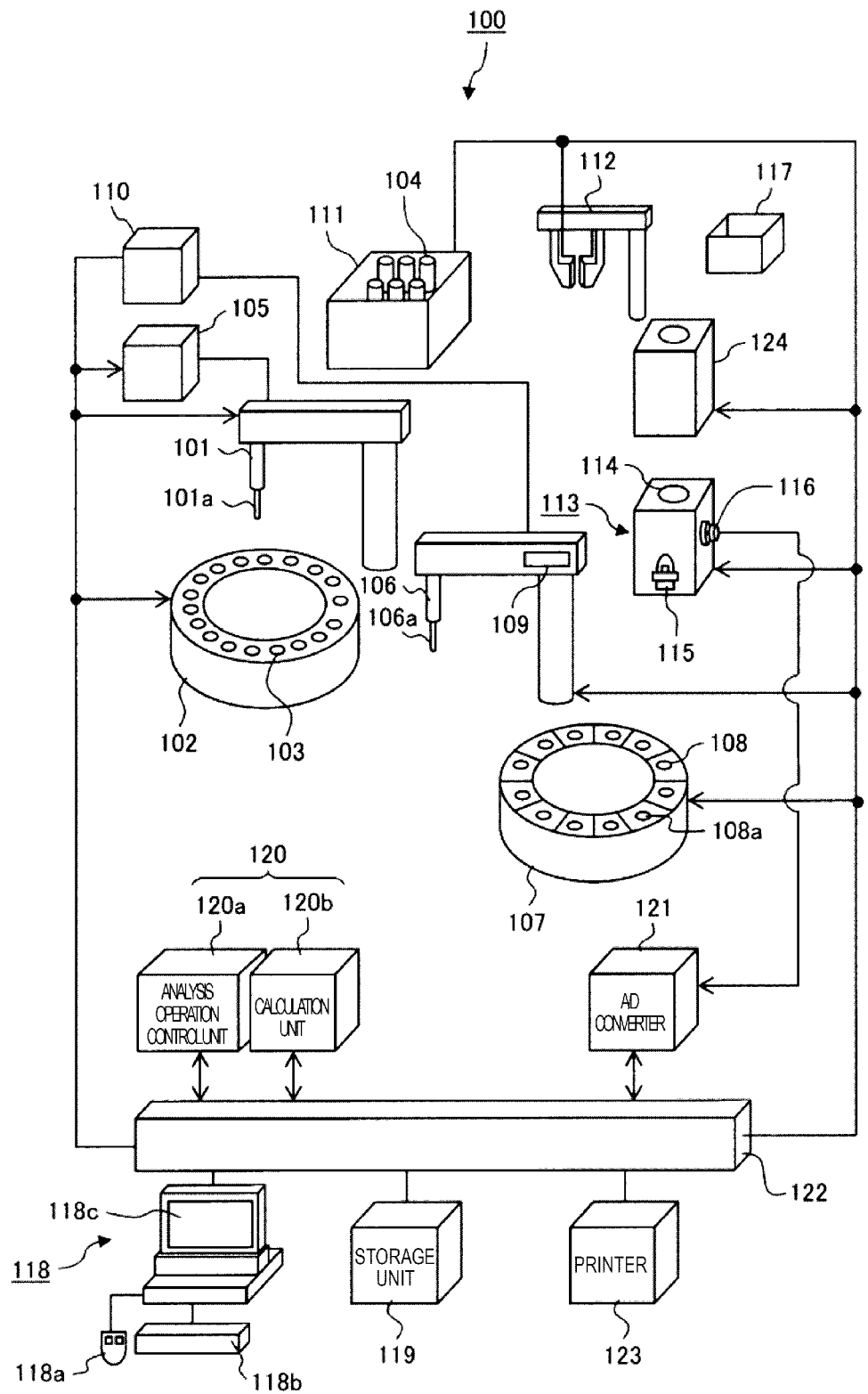

[Fig. 2]
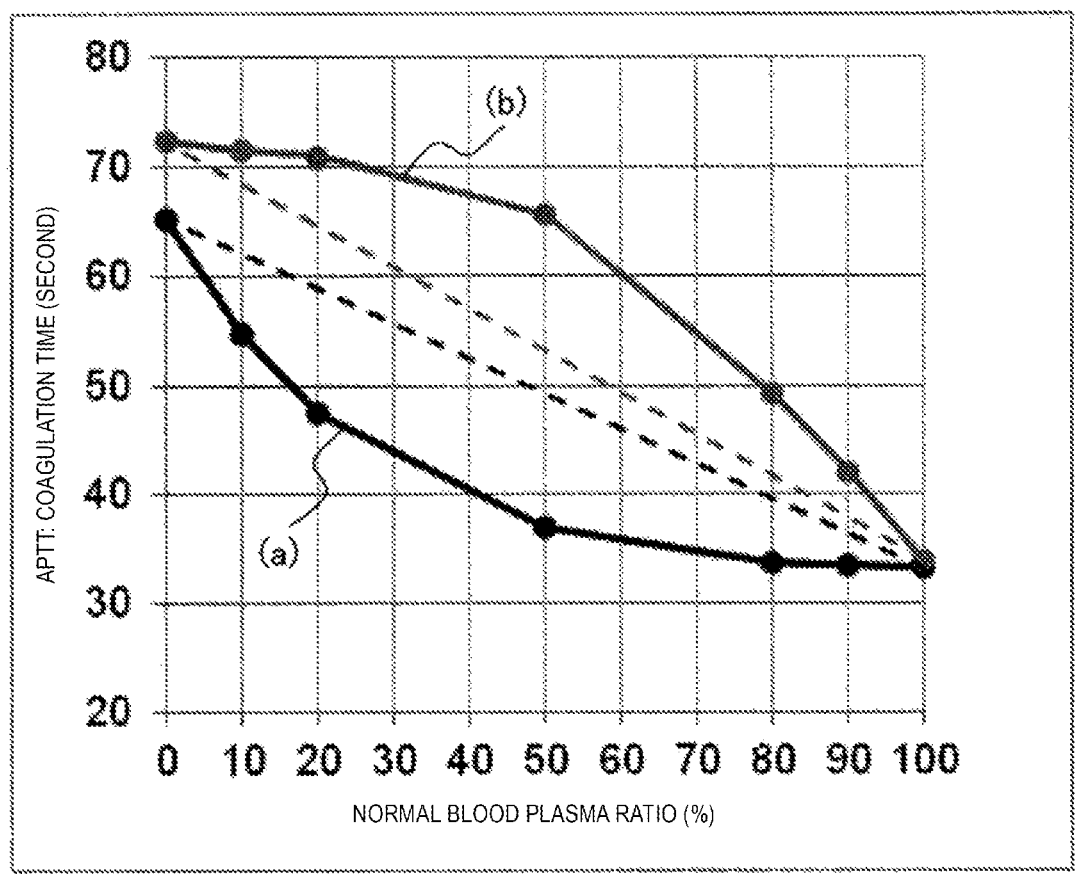

[Fig. 3]
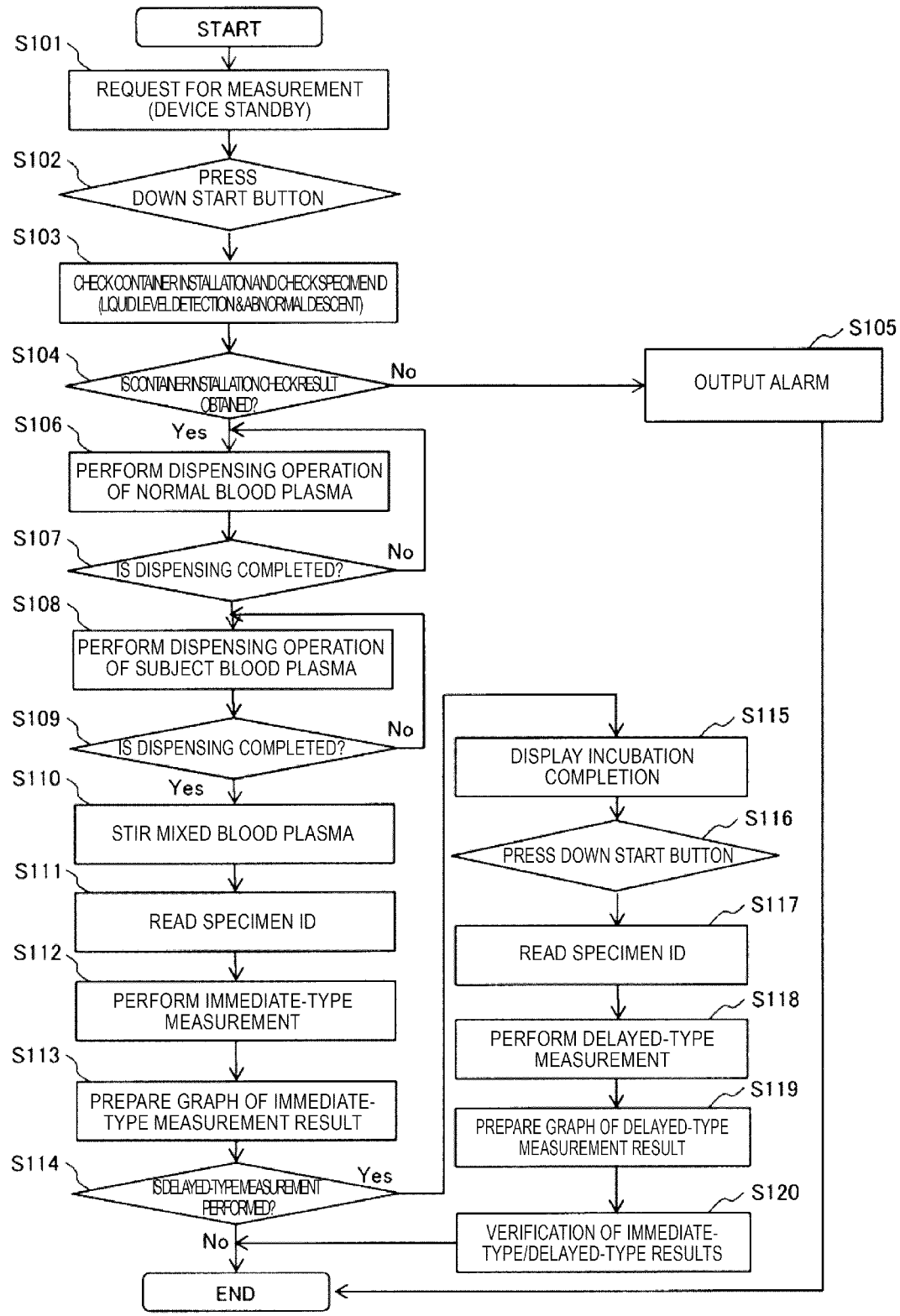

[Fig. 4]

[Fig. 5]
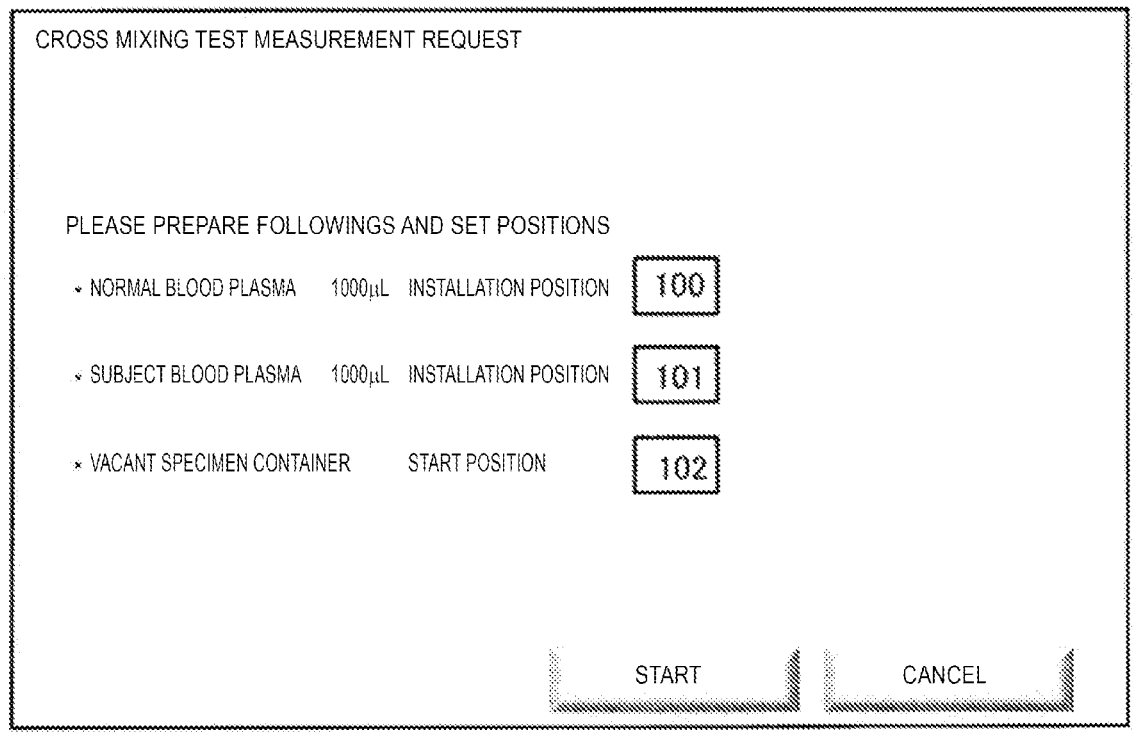
[Fig. 6]
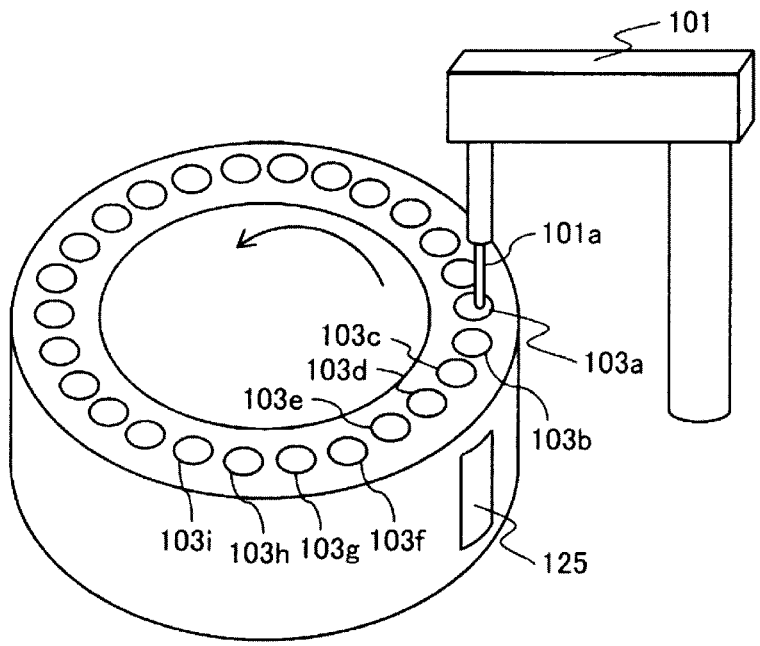

[Fig. 7]
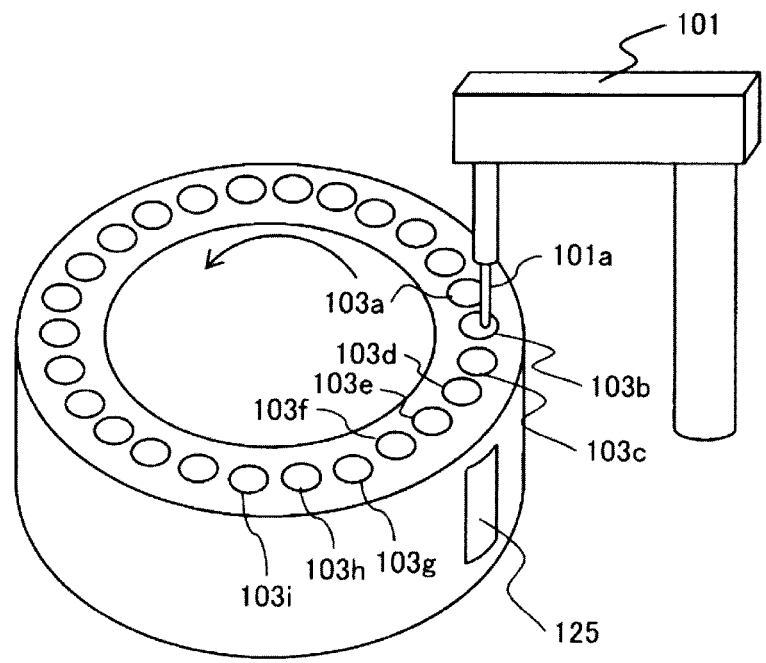
[Fig. 8]
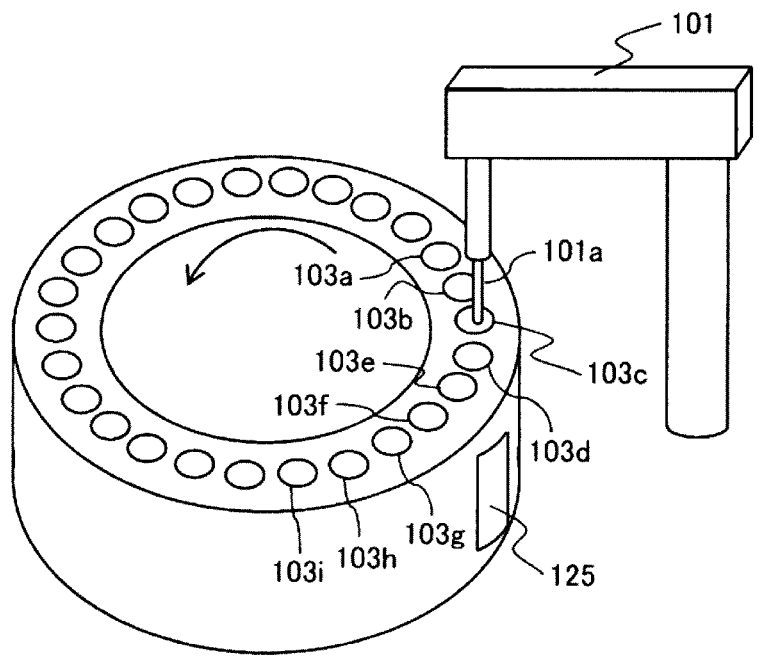

[Fig. 9]
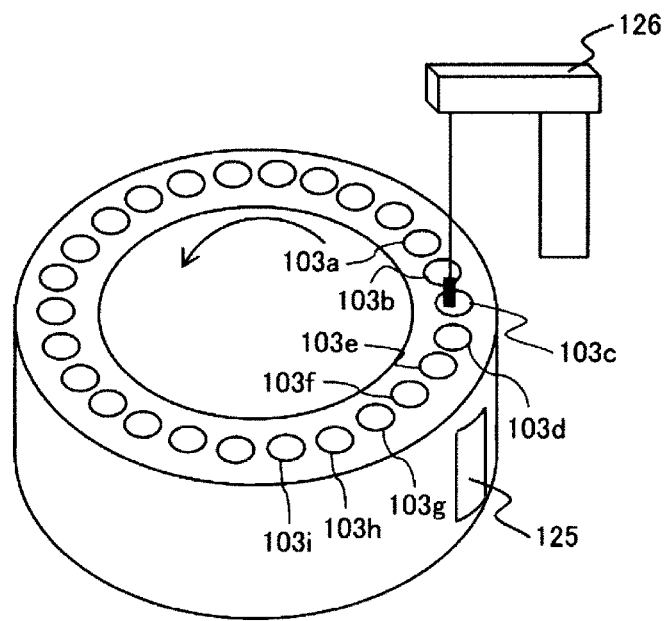

[Fig. 10]
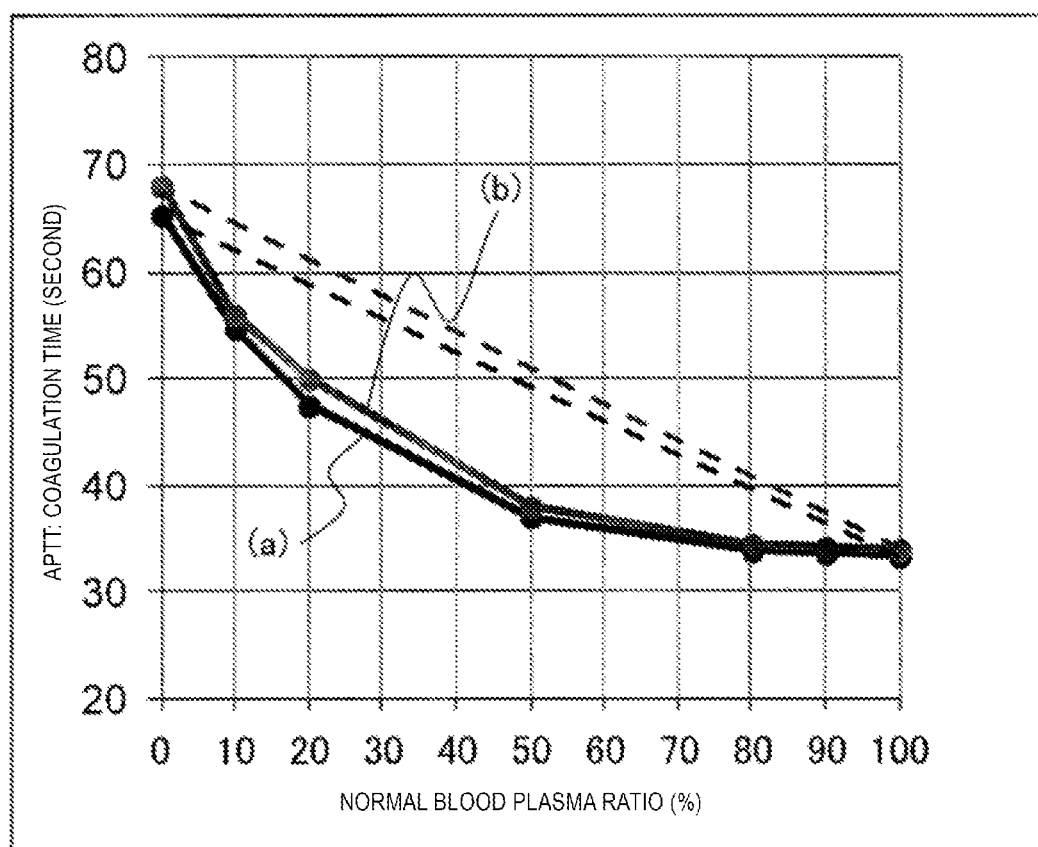

[Fig. 11]
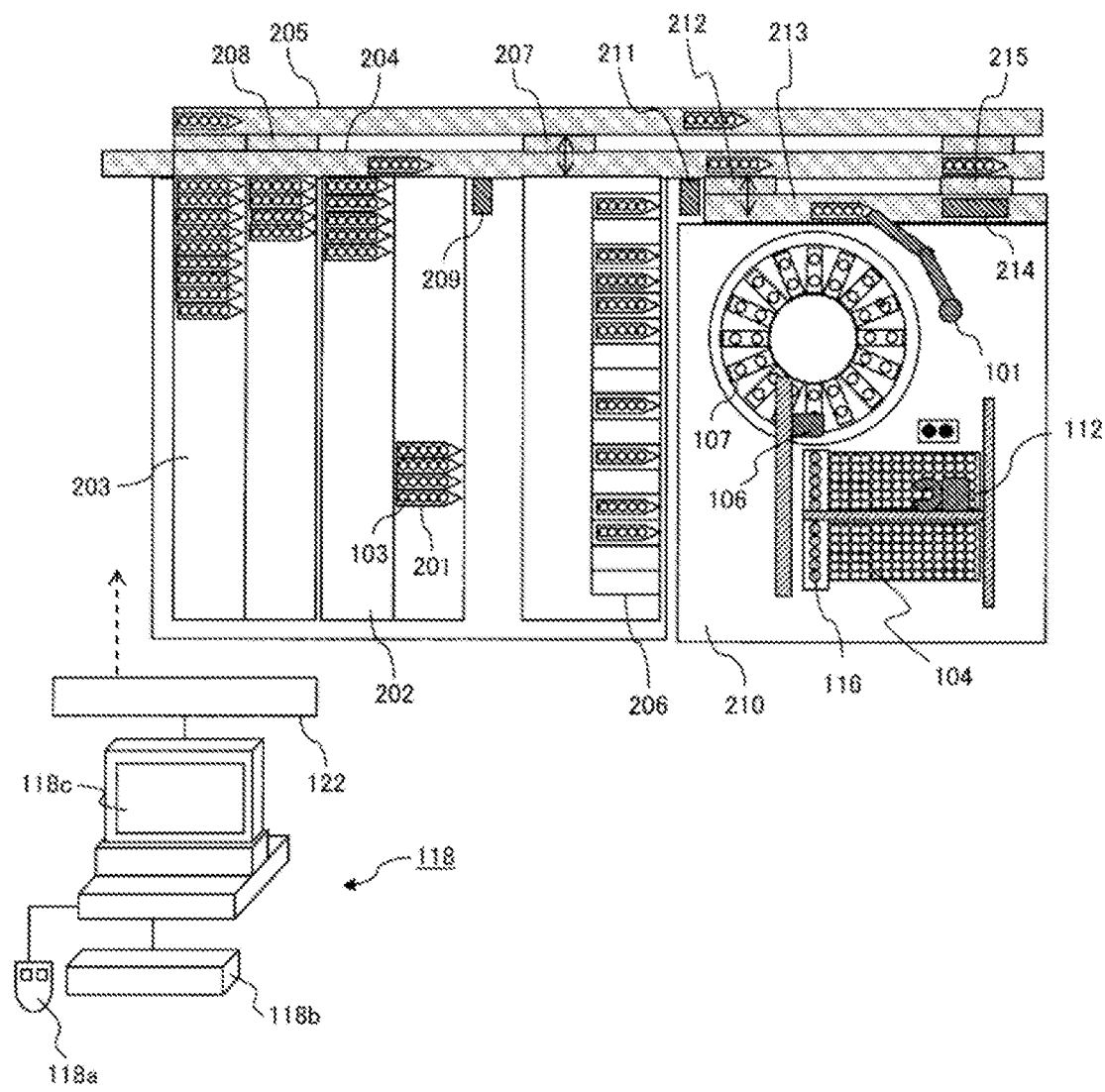

[Fig. 12]
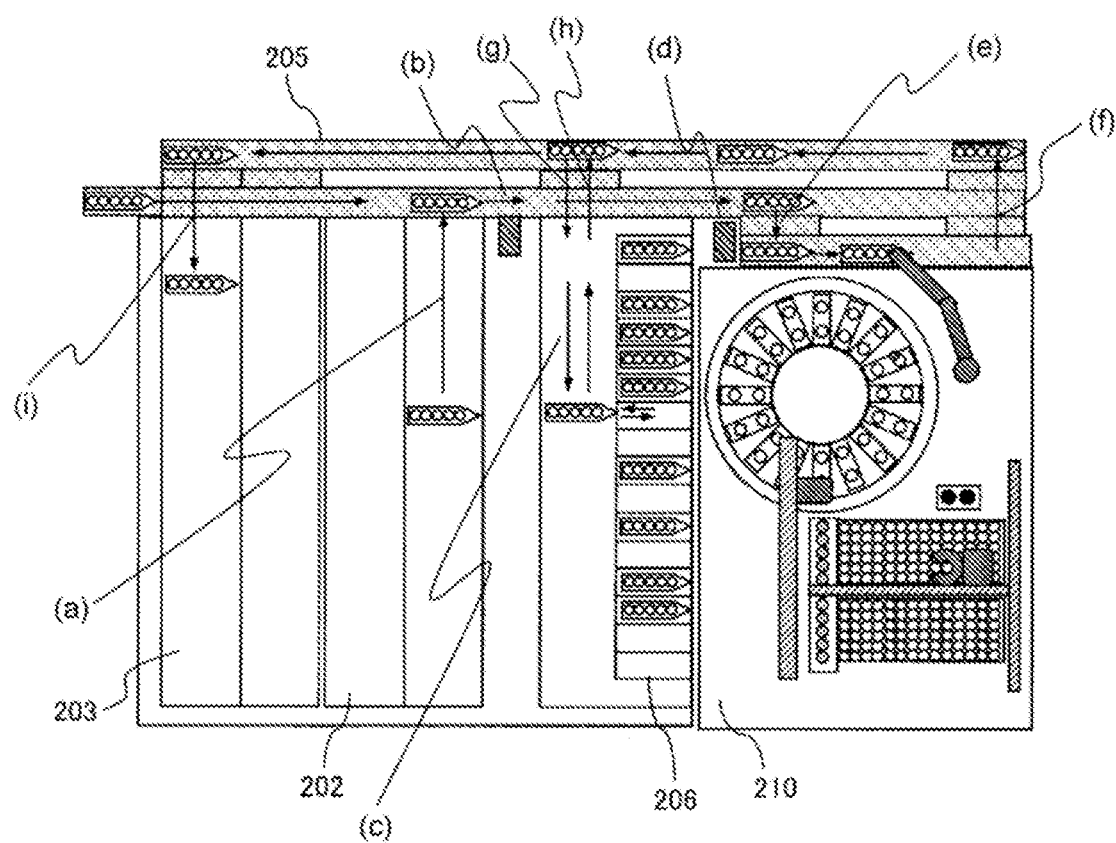

[Fig. 13]
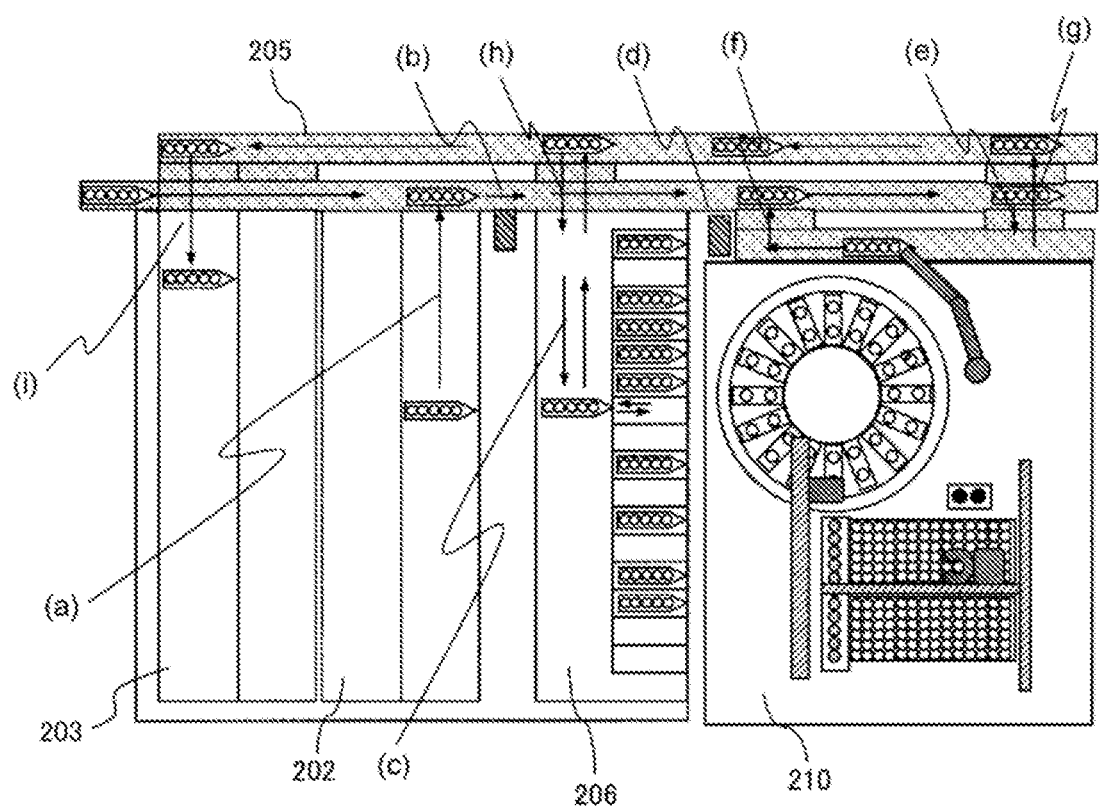

[Fig. 14]
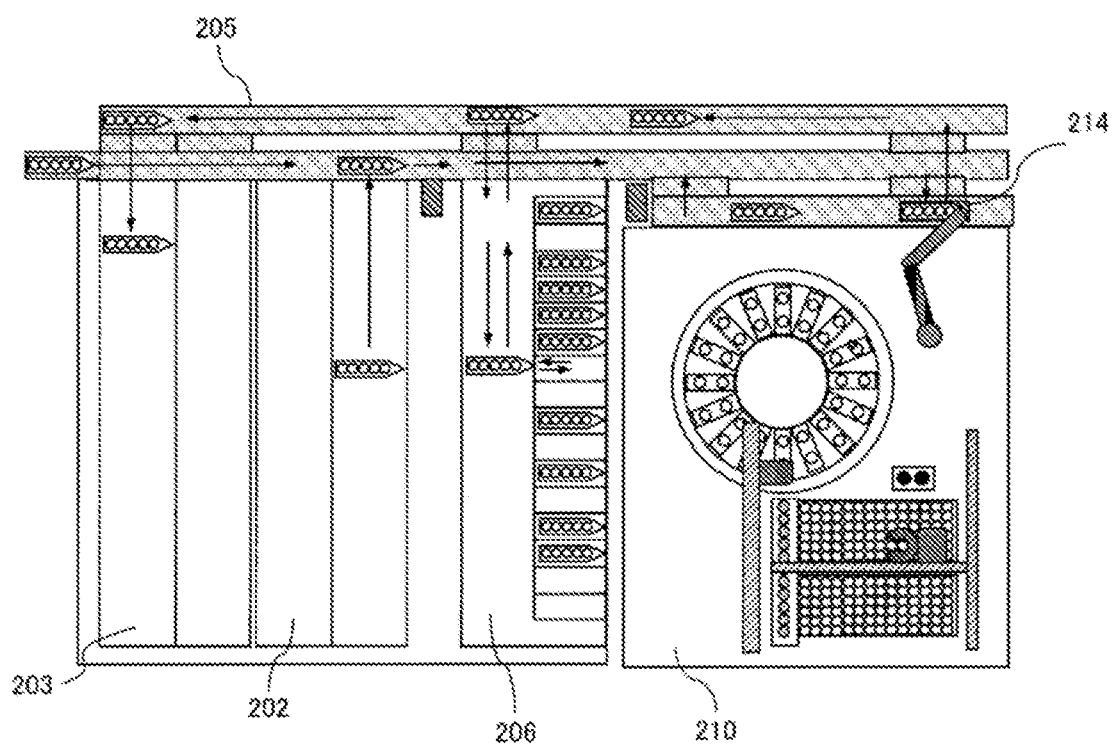

[Fig. 15]
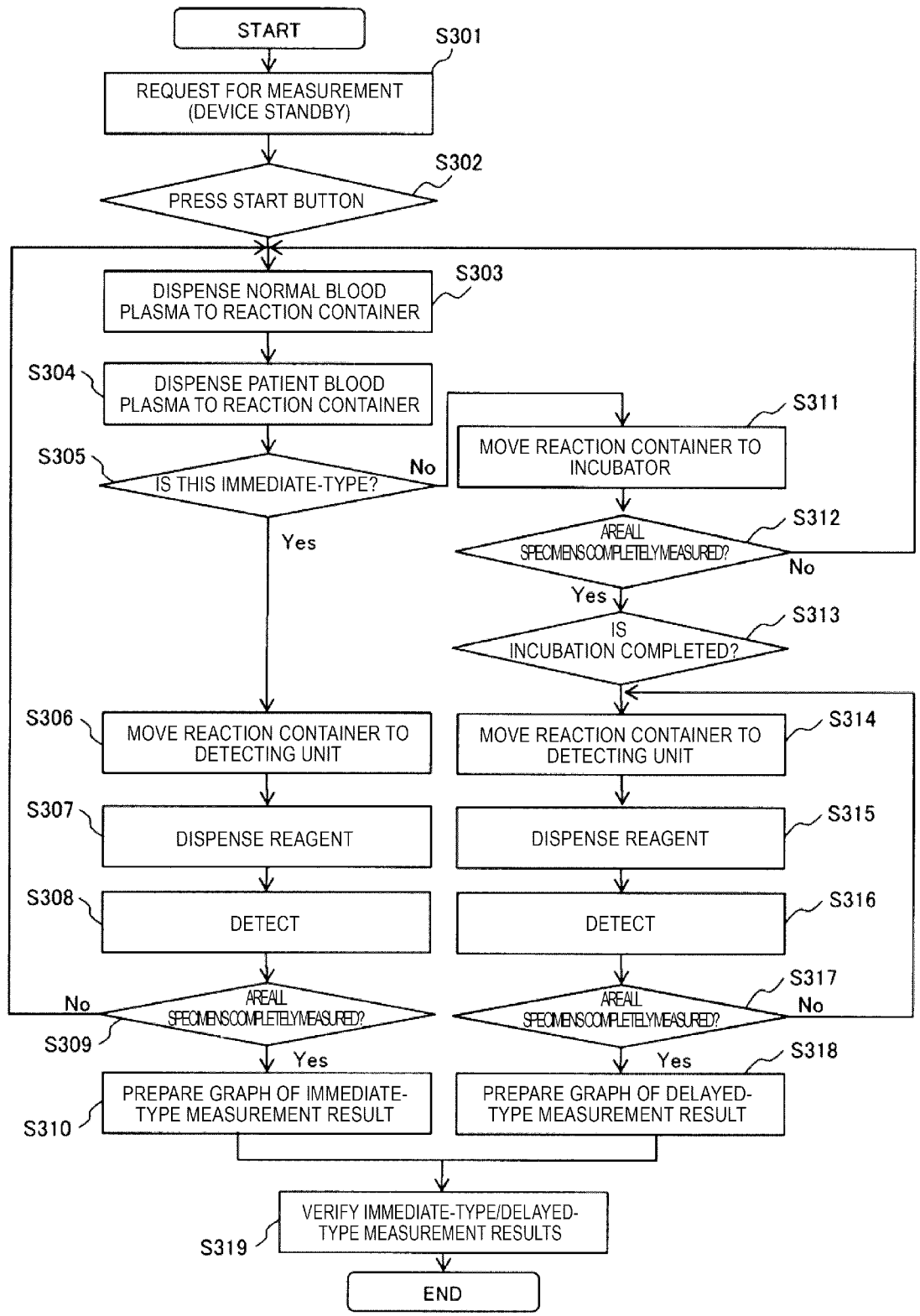

[Fig. 16]

[Fig. 17]
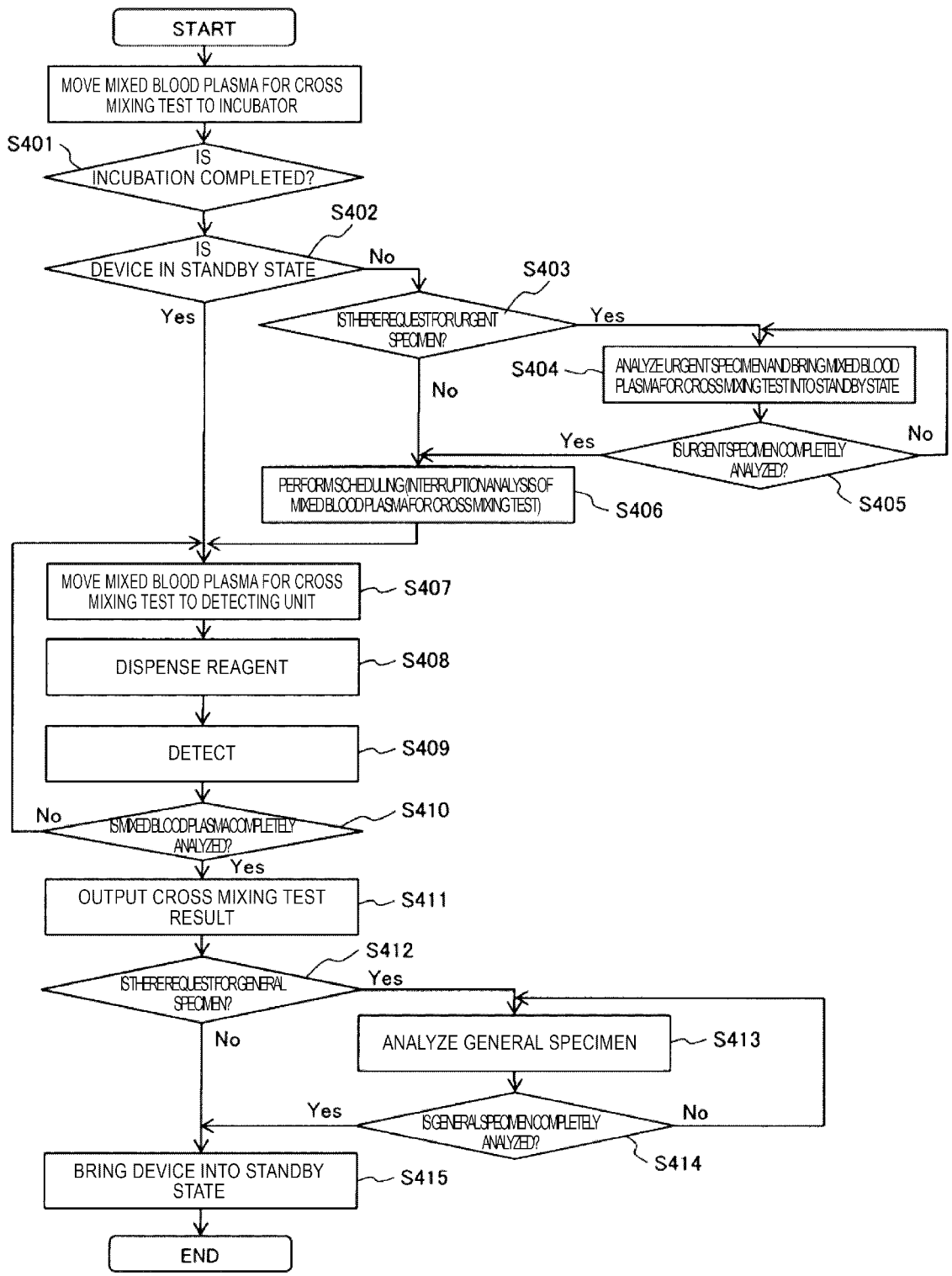

[Fig. 18]
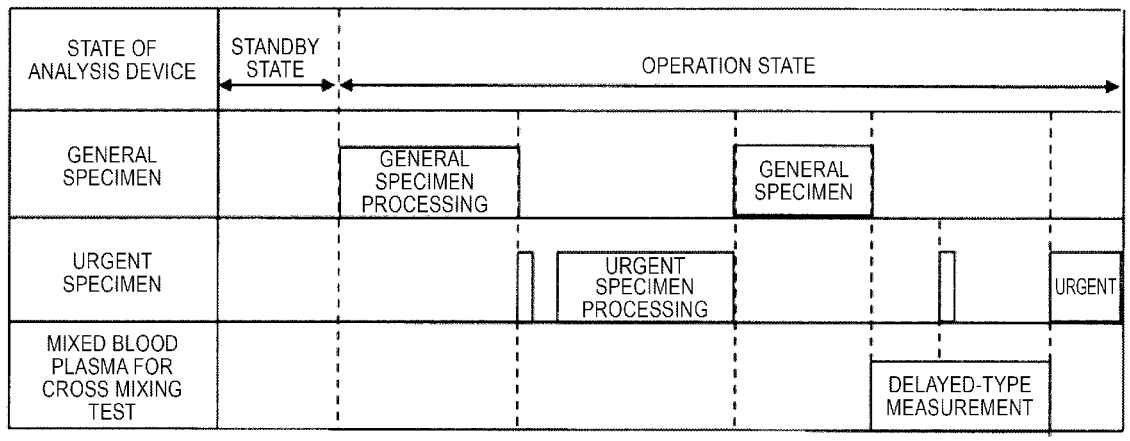
[Fig. 19]
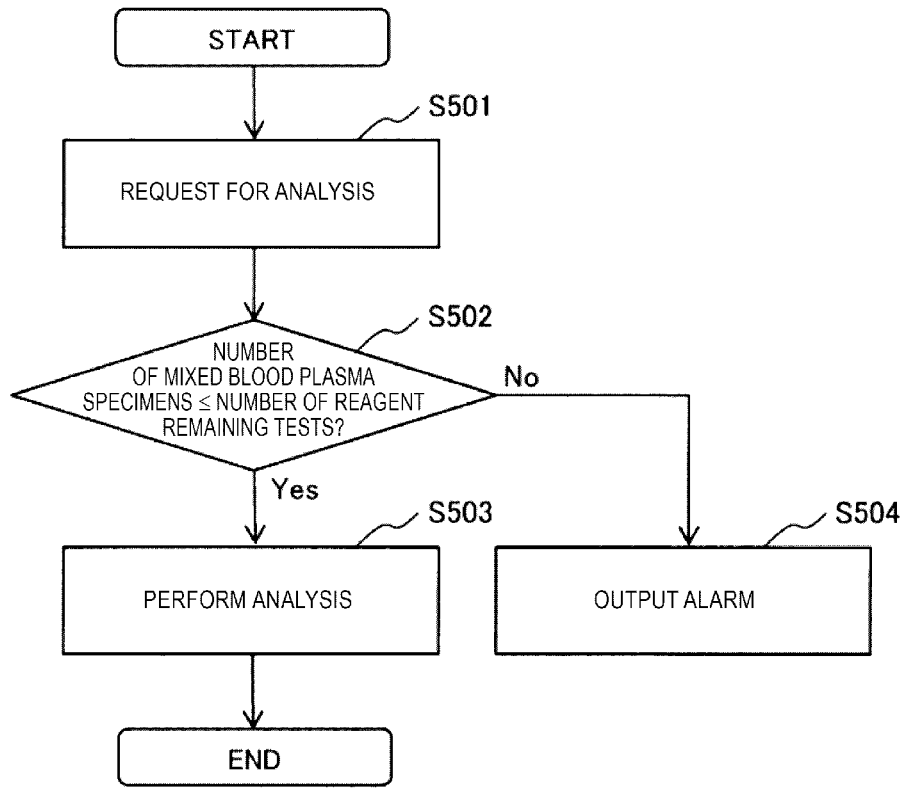

[Fig. 20]
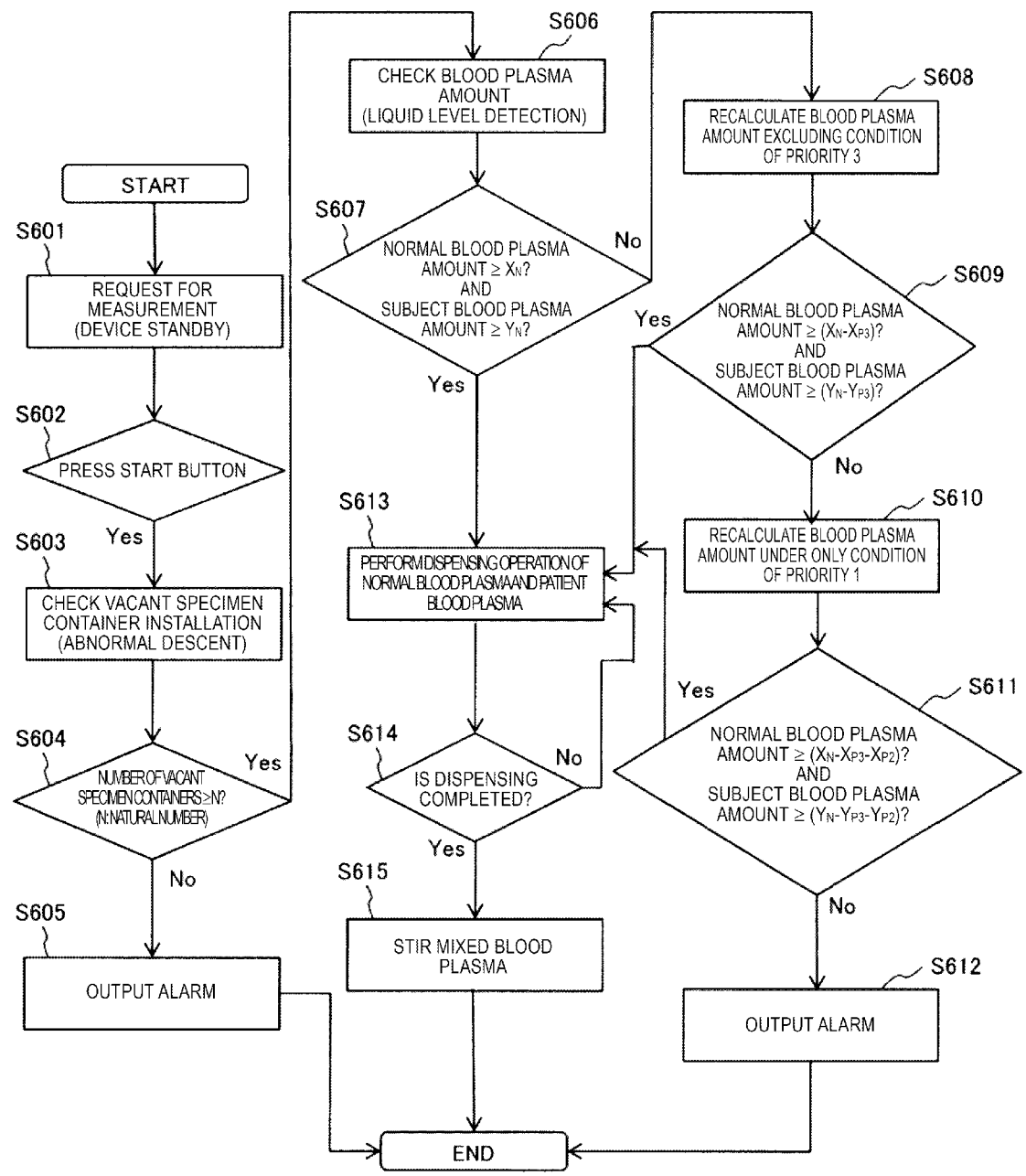

[Fig. 21]

```
CROSS MIXING TEST MEASUREMENT REQUEST        NORMAL BLOOD PLASMA
                                                 RATIO SETTING
 ● GENERAL                                       SELECT ALL  ☑
 ○ URGENT    SUBJECT ID  [          ]
 ○ CONTROL                                       PRIORITY SETTING

┌─────┬─────┬─────┬─────┬─────┐      ☑    0   %    [ 1 ]
  │ PT  │APTT │ Fbg │ TTO │ Hpt │      ☑   10   %    [ 2 ]
  ├─────┼─────┼─────┼─────┼─────┤      ☑   20   %    [ 2 ]
  │ATIII│ DD  │ FDP │     │     │      ☑   50   %    [ 1 ]
  ├─────┼─────┼─────┼─────┼─────┤      ☑   80   %    [ 3 ]
  │     │     │     │     │     │      ☑   90   %    [ 3 ]
  ├─────┼─────┼─────┼─────┼─────┤      ☑  100   %    [ 1 ]
  │     │     │     │     │     │
  └─────┴─────┴─────┴─────┴─────┘
         ~127              [ NEXT ]           [ CANCEL ]
```

[Fig. 22]

| NORMAL BLOOD PLASMA RATIO | 0% | 10% | 20% | 50% | 80% | 90% | 100% | TOTAL |
|---|---|---|---|---|---|---|---|---|
| NORMAL BLOOD PLASMA AMOUNT (μL) | 0 | 20 | 40 | 100 | 160 | 180 | 200 | 700 |
| SUBJECT BLOOD PLASMA AMOUNT (μL) | 200 | 180 | 160 | 100 | 40 | 20 | 0 | 700 |

[Fig. 23]

| NORMAL BLOOD PLASMA RATIO | 0% | 10% | 20% | 50% | 100% | TOTAL |
|---|---|---|---|---|---|---|
| NORMAL BLOOD PLASMA AMOUNT (μL) | 0 | 20 | 40 | 100 | 200 | 360 |
| SUBJECT BLOOD PLASMA AMOUNT (μL) | 200 | 180 | 160 | 100 | 0 | 640 |

[Fig. 24]

| NORMAL BLOOD PLASMA RATIO | 0% | 50% | 100% | TOTAL |
|---|---|---|---|---|
| NORMAL BLOOD PLASMA AMOUNT (μL) | 0 | 100 | 200 | 300 |
| SUBJECT BLOOD PLASMA AMOUNT (μL) | 200 | 100 | 0 | 300 |

AUTOMATIC ANALYSIS DEVICE AND AUTOMATIC ANALYSIS METHOD

TECHNICAL FIELD

The present invention relates to an automatic analysis device for carrying out qualitative/quantitative analyses of biological samples such as blood and urine, and particularly relates to an automatic analysis device and an automatic analysis method which are suitably used for blood coagulation/hemostasis tests.

BACKGROUND ART

Blood coagulation tests are carried out in order to recognize the pathology of a blood coagulation fibrinolysis system, to diagnose a disseminated intravascular coagulation syndrome (DIC), to confirm a thrombus treatment effect, and to diagnose hemophilia. In particular, as for blood coagulation time measurement, a time until a fibrin clot is formed after a specimen and a reagent are mixed with each other (hereinafter, referred to as a blood coagulation time) is measured. In a case where there is a congenital or acquired abnormality, the blood coagulation time is prolonged.

However, if the blood coagulation time is merely measured, it is not possible to determine whether the cause of the abnormality is activity degradation resulting from blood coagulation factor deficiency (deficiency type), or whether the cause of the abnormality is activity degradation resulting from blood coagulation reaction inhibition (inhibitor type) of an antibody with respect to a component configuring a blood coagulation system or a component in a blood coagulation time measurement reagent.

On the other hand, in a case of treatment, it is necessary to clarify the cause of the abnormality, since a treatment policy varies depending on whether the cause of the prolonged blood coagulation time is the deficiency type or the inhibitor type.

As a method for determining the cause of the prolonged blood coagulation time, there is a cross mixing test (also called a blood coagulation correction test or a cross-flow-over test) using added normal blood plasma. In the cross mixing test, the normal blood plasma is added to subject blood plasma, and a correction degree of the blood coagulation time is graphed and determined. As the most representative application example of the cross mixing test, a factor of prolonged APTT is determined. However, in some cases, items such as prothrombin time (PT), dilute PT (dPT), dilute APTT (dAPTT), kaolin coagulation time (KCT), and dilute Russell's viper venom time (dRVVT) are performed.

Incidentally, although APTT is a major item that can be performed in most facilities for carrying out the blood coagulation tests, a current situation hardly shows that the cross mixing test is frequently carried out. In a case where APTT cannot be performed in the facilities and an outsourcer is requested to carry out the test, it takes time to receive results, thereby leading to delayed discovery and delayed treatment start of severe diseases such as haemophilia. The reason why this situation occurs is that preparation and incubation work of a specimen is complicated and interpretation of the result is not clear. Consequently, the work requires a tester's skill job.

In order to solve the above-described problem, PTL 1 proposes the following technique. According to PTL 1, each blood coagulation time is measured for subject blood plasma alone, normal blood plasma alone, and a sample (mixed blood plasma) obtained by mixing the subject blood plasma and the normal blood plasma at least at one mixing ratio. A difference is obtained between a lower area (A) of a line graph in which an obtained measured value is plotted and a lower area (B) of a straight line connecting measured values of the subject blood plasma alone and the normal blood plasma alone. An area ratio (A−B)/(B) of the difference is compared with a predetermined reference area ratio Y. Based on the comparison result, it is determined whether the cause is the inhibitor type or the deficiency type.

CITATION LIST

Patent Literature

PTL 1: Pamphlet of International Publication No. WO2009/153964

SUMMARY OF INVENTION

Technical Problem

However, PTL 1 does not disclose a method for automated mixing of the subject blood plasma and the normal blood plasma. In a case the mixing is prepared by a hand using method, work may be complicated, or the accuracy of the mixing ratio of the obtained mixed blood plasma may vary depending on a worker's skill level.

Therefore, the present invention aims to provide an automatic analysis device and an automatic analysis method which enable automated preparation of the mixed blood plasma obtained by mixing the subject blood plasma and the normal blood plasma at a prescribed mixing ratio.

Solution to Problem

In order to solve the above-described problem, according to the present invention, there is provided an automatic analysis device which includes a specimen container holding unit that accommodates and holds a plurality of specimen containers, a specimen dispensing mechanism that dispenses subject blood plasma and/or normal blood plasma to be added to correct a coagulation time of the subject blood plasma, to a vacant specimen container in the plurality of specimen containers accommodated in the specimen container holding unit, a reaction container in which the subject blood plasma alone, the normal blood plasma alone, and mixed blood plasma obtained by mixing the subject blood plasma and the normal blood plasma at least at one mixing ratio are prepared inside the specimen container, and in which the subject blood plasma, the normal blood plasma, and the mixed blood plasma which are prepared are dispensed by the specimen dispensing mechanism, a reagent dispensing mechanism that dispenses a reagent to the reaction container, and a measurement unit that irradiates the subject blood plasma to which the reagent inside the reaction container is added, the normal blood plasma and/or the mixed blood plasma with light emitted from a light source, and that measures the coagulation time, based on obtained scattered light and/or transmitted light.

In addition, according to the present invention, there is provided an automatic analysis method of an automatic analysis device which has at least a specimen container holding unit that accommodates and holds a plurality of specimen containers, a specimen dispensing mechanism, a reagent dispensing mechanism, and a measurement unit. The automatic analysis method includes causing the specimen dispensing mechanism to dispense subject blood plasma and/or normal blood plasma to be added to correct a coagulation time of the subject blood plasma, to a vacant specimen container in a plurality of specimen containers accommodated in the specimen container holding unit, preparing the subject blood plasma alone, the normal blood plasma alone, and mixed blood plasma obtained by mixing the subject blood plasma and the normal blood plasma at least at one mixing ratio, inside the specimen container, causing a reaction container to contain the subject blood plasma, the normal blood plasma, and the mixed blood plasma which are prepared, and causing the reagent dispensing mechanism to dispense a reagent to the reaction container, and irradiating the subject blood plasma to which the reagent inside the reaction container is added, the normal blood plasma and/or the mixed blood plasma with light emitted from a light source, and measuring the coagulation time, based on obtained scattered light and/or transmitted light.

Advantageous Effects of Invention

According to the present invention, it is possible to provide an automatic analysis device and an automatic analysis method which enable automated preparation of mixed blood plasma obtained by mixing subject blood plasma and normal blood plasma at a prescribed mixing ratio.

Problems, configurations, and advantageous effects other than those described above will be clarified by the description of the following embodiments.

BRIEF DESCRIPTION OF DRAWINGS

FIG. 1 is an overall schematic configuration diagram of an automatic analysis device in Embodiment 1 according to an embodiment of the present invention.

FIG. 2 is a schematic view of a cross mixing test.

FIG. 3 is a flowchart illustrating a process flow of the automatic analysis device illustrated in FIG. 1.

FIG. 4 illustrates a display example of an operation screen when a measurement is requested in the cross mixing test.

FIG. 5 illustrates a display example of an operation screen when a measurement is requested in the cross mixing test.

FIG. 6 is a view illustrating a state where normal blood plasma is aspirated by a specimen dispensing mechanism.

FIG. 7 is a view illustrating a state where subject blood plasma is aspirated by the specimen dispensing mechanism.

FIG. 8 is a view illustrating a state where the normal blood plasma or the subject blood plasma is discharged by the specimen dispensing mechanism.

FIG. 9 is a view illustrating a state where mixed blood plasma is stirred by a stirring mechanism.

FIG. 10 is a view illustrating a result of the cross mixing test carried out by the automatic analysis device according to Example 1.

FIG. 11 is an overall schematic configuration diagram of an automatic analysis device in Example 2 according to another embodiment of the present invention.

FIG. 12 is a view for describing a transportation procedure of specimen racks in the automatic analysis device illustrated in FIG. 11.

FIG. 13 is a view for describing a transportation procedure of specimen racks during a cross mixing test in the automatic analysis device illustrated in FIG. 11.

FIG. 14 is a view for describing a specimen dispensing position during the cross mixing test in the automatic analysis device illustrated in FIG. 11.

FIG. 15 is a flowchart illustrating a process flow of an automatic analysis device in Example 3 according to another embodiment of the present invention.

FIG. 16 illustrates a display example of an operation screen when a measurement is requested in a cross mixing test according to Example 3.

FIG. 17 is a flowchart illustrating a process flow of an automatic analysis device in Example 4 according to another embodiment of the present invention.

FIG. 18 is a timing chart illustrating an operation of the automatic analysis device according to Example 4.

FIG. 19 is a flowchart illustrating a process flow of an automatic analysis device in Example 5 according to another embodiment of the present invention.

FIG. 20 is a flowchart illustrating a process flow of an automatic analysis device in Example 6 according to another embodiment of the present invention.

FIG. 21 illustrates a display example of an operation screen when a measurement is requested in a cross mixing test according to Example 6.

FIG. 22 is a view illustrating normal blood plasma alone, subject blood plasma alone, and mixed blood plasma obtained at five different mixing ratios.

FIG. 23 is a view illustrating normal blood plasma alone, subject blood plasma alone, and mixed blood plasma obtained at three different mixing ratios.

FIG. 24 is a view illustrating normal blood plasma alone, subject blood plasma alone, and mixed blood plasma obtained at one mixing ratio.

DESCRIPTION OF EMBODIMENTS

In the present specification, "subject blood plasma" includes both blood plasma of an inpatient or outpatient and blood plasma of a subject in medical examinations. In addition, in the present specification, "normal blood plasma", "subject blood plasma", and "mixed blood plasma mixed at various mixing ratios" are collectively referred to as a specimen for measuring a blood coagulation time, in some cases. In addition, in the present specification, a "general specimen" is a specimen of the subject.

FIG. 2 is a schematic view of a cross mixing test. Normal blood plasma is added to subject blood plasma, and both of these are mixed to prepare a specimen so that ratios of the normal blood plasma are respectively 0%, 10%, 20%, 50%, 80%, 90%, and 100%, thereby measuring APTT. A relationship between a measurement result (blood coagulation time) and the ratios of the normal blood plasma is plotted, thereby preparing a graph. As illustrated in FIG. 2, a horizontal axis represents a normal blood plasma ratio (%), and a vertical axis represents an activated partial thromboplastin time (APTT: blood coagulation time). For example, in a deficiency type as illustrated by a solid line (a) in FIG. 2, APTT prolongation is corrected by adding the normal blood plasma, and the deficiency type shows a pattern protruding downward. On the other hand, in an inhibitor type as illustrated by a solid line (b) in FIG. 2, even if the normal blood plasma is added, APTT prolongation is less likely to be corrected, and the inhibitor type shows a pattern protruding upward. However, reaction of an inhibitor to a factor VIII depends on a time and a temperature. Accordingly, reaction immediately after blending (mixing) (hereinafter, referred to as immediate reaction) does not clearly show the shape protruding upward. Reaction after incubating for a prescribed period of time at 37° C. (hereinafter, referred to as delayed reaction) shows the shape protruding upward in some cases.

Therefore, measurements for both the immediate reaction and the delayed reaction are recommended in the cross mixing test.

Hereinafter, embodiments according to the present invention will be described with reference to the drawings.

Example 1

FIG. 1 is an overall schematic configuration diagram of an automatic analysis device in Example 1 according to an embodiment of the present invention. Here, a flow of a basic blood coagulation test will be described with reference to FIG. 1. However, the embodiment is not limited to the following example.

An automatic analysis device 100 is schematically configured to include a specimen dispensing mechanism 101, a specimen disc 102, a reagent dispensing mechanism 106, a reagent disc 107, a reaction container stock unit 111, a reaction container transport mechanism 112, a detecting unit 113, a reaction container disposal unit 117, an operation unit 118, a storage unit 119, and a control unit 120.

The specimen dispensing mechanism 101 aspirates a specimen contained in the specimen container 103 disposed in the specimen disc 102 rotating clockwise and counter-clockwise, and discharges the specimen to the reaction container 104 accommodated in the reaction container stock unit 111. The specimen dispensing mechanism 101 includes a specimen dispensing probe 101a in a distal portion, and performs an aspiration operation and a discharge operation of the specimen by operating a specimen syringe pump 105 controlled by the control unit 120.

The reagent dispensing mechanism 106 aspirates the reagent contained in the reagent container 108 disposed in the reagent disc 107, and discharges the reagent to the reaction container 104 accommodated in the reaction container stock unit 111. The reagent dispensing mechanism 106 includes a reagent dispensing probe 106a in a distal portion, and performs an aspiration operation and a discharge operation of the reagent by operating a reagent syringe pump 110 controlled by the control unit 120.

In addition, the reagent dispensing mechanism 106 is internally equipped with a reagent temperature raising mechanism 109. The temperature of the reagent aspirated by the reagent dispensing mechanism 106 is raised to an appropriate temperature (predetermined temperature) by the reagent temperature raising mechanism 109 controlled by the control unit 120.

The reaction container transport mechanism 112 transports and installs the reaction container 104 accommodated in the reaction container stock unit 111. The reaction container transport mechanism 112 grips the reaction container 104 and pivots in an arc shape in a horizontal plane. In this manner, the reaction container 104 is transported from the reaction container stock unit 111, and is installed in the reaction container installation unit 114 of the detecting unit 113.

The detecting unit 113 has at least one or more reaction container installation units 114 for mounting the reaction container 104 thereon. The detecting unit 113 measures light intensity of the specimen inside the reaction container 104 inserted into the reaction container installation unit 114. Although the present embodiment shows a case where one detecting unit 113 is provided, a configuration having a plurality of detecting units 113 may be adopted. An example of detection principles in the detecting unit 113 will be described below. Light irradiated from a light source 115 is scattered by a reaction solution inside the reaction container 104. A detector (light receiving unit) 116 is configured to include a photodiode. The detector 116 receives the scattered light scattered by the reaction solution (specimen) inside the reaction container 104, and performs light/electric conversion, thereby outputting a light measurement signal indicating the intensity of the received scattered light to an A/D converter 121. The measurement signal of the scattered light subjected to A/D conversion in by the A/D converter 121 is input to the control unit 120 via an interface 122. The operation of the detecting unit 113 is controlled by the control unit 120. Here, the control unit 120 is configured to include an analysis operation control unit 120a and a calculation unit 120b. For example, the analysis operation control unit 120a and the calculation unit 120b are realized by a processor such as a CPU, read various programs stored in a ROM or the storage unit 119 (not illustrated), and execute the read program, thereby performing control and calculation.

That is, the analysis operation control unit 120a controls the specimen dispensing mechanism 101 and the specimen disc 102 so as to dispense the specimen. In addition, the analysis operation control unit 120a controls the reagent dispensing mechanism 106 and the reagent disc 107 so as to discharge the reagent to the specimen inside the reaction container 104. Furthermore, the analysis operation control unit 120a controls the operation of the automatic analysis device such as the movement of the reaction container 104 and the disposal of the reaction container 104.

Based on a result of comparison between a signal value obtained from a measurement value of the light intensity changing in a time-dependent manner according to a degree of mixed reaction of the specimen and the reagent and a predetermined determination threshold value, the calculation unit 120b performs a measurement process for measuring a reaction time of the specimen. The calculated coagulation time is output to a display unit 118c, and is stored in the storage unit 119. The coagulation time as the calculation result may be printed out by a printer 123 via the interface 122.

The detector 116 is not limited to a configuration which receives the scattered light scattered by the reaction solution (specimen) inside the reaction container 104. For example, the detector 116 may be configured to detect the intensity of transmitted light which passes through the reaction solution (specimen) inside the reaction container 104. In addition, the detector 116 may use both a detecting method of the scattered light and a detecting method of the transmitted light. Furthermore, in addition to the above-described configurations, the detector 116 may utilize viscosity.

The reaction container transport mechanism 112 grips the reaction container 104 which is completely measured, and discards the reaction container 104 to the reaction container disposal unit 117.

In order to improve the throughput, a configuration having no detector may be adopted which includes an incubator 124 for warming the specimen before a measurement start reagent is added.

Analysis items of the specimen analyzed by the automatic analysis device 100 are input from the operation unit 118 to the control unit 120 via a keyboard 118b serving as an input unit or an operation screen displayed on the display unit 118c. A configuration may be adopted which uses a graphical user interface (GUI) for inputting the analysis items by causing a mouse 118a to perform a pointing operation on the analysis items displayed on the display unit 118c with a pointer.

For the sake of convenience in illustrating all configuration elements, FIG. 1 illustrates an arrangement where the reaction container stock unit 111, the specimen disc 102, and the reagent disc 107 are separated from each other. However, the specimen disc 102 and the reaction container stock unit 111 are arranged within a range of an arc-shaped movement trajectory inside a horizontal plane of the specimen dispensing probe 101a configuring the specimen dispensing mechanism 101. The reagent disc 107 and the reaction container stock unit 111 are arranged within a range of an arc-shaped movement trajectory inside the horizontal plane of the reagent dispensing probe 106a configuring the reagent dispensing mechanism 106. Therefore, in a case where all of these are viewed from above, the specimen disc 102, the reaction container stock unit 111, and the reagent disc 107 are arranged in a substantially triangular shape.

Subsequently, a request for the cross mixing test and a preparation method of the specimen in the automatic analysis device 100 of this embodiment will be described in detail below. FIG. 3 is a flowchart illustrating a process flow of the automatic analysis device illustrated in FIG. 1, and particularly illustrates a flow of the preparation method of the specimen when the measurement is requested in the cross mixing test.

First, the automatic analysis device 100 receives the request for the cross mixing test (Step S101). A method of receiving the request includes a method of receiving the request via a network system using a host computer and a method of receiving a cross mixing test measurement request input by an operator who requests the measurement request through the operation unit 118. In the following description, a case where the measurement request is input via the operation screen will be described as an example.

Figure 4:
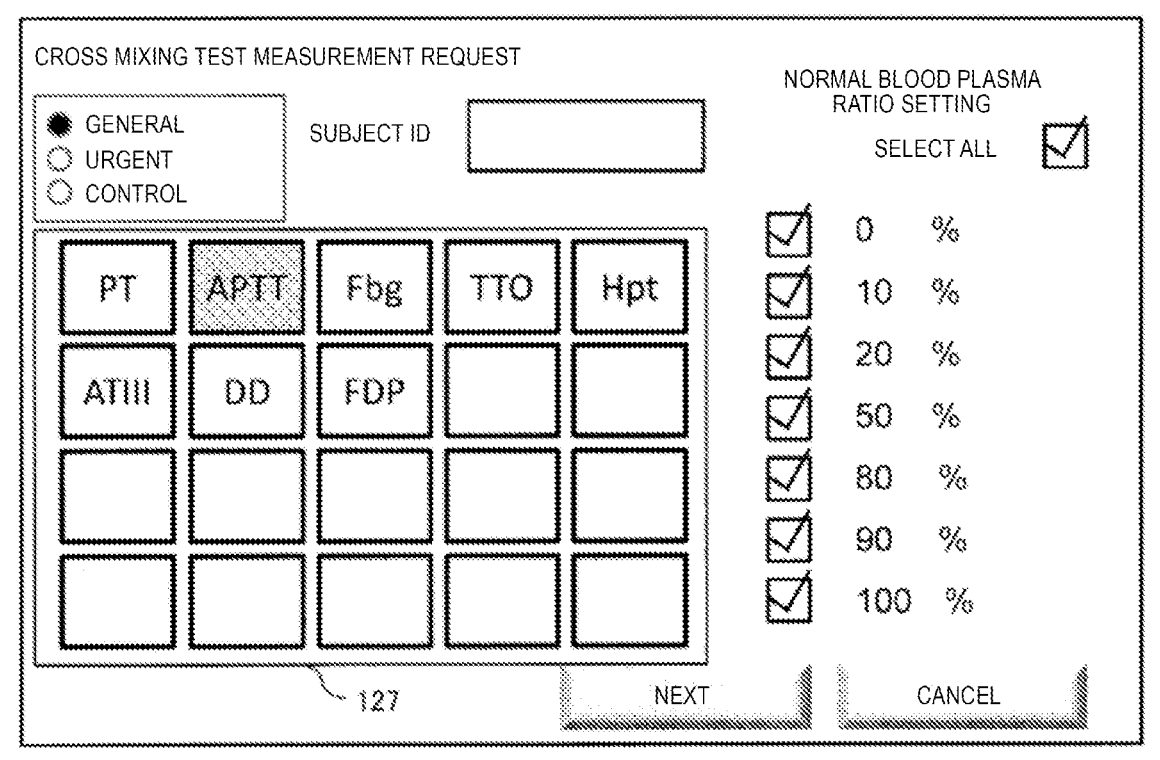

FIGS. 4 and 5 illustrate a display example of the operation screen displayed on the display unit 108c configuring the operation unit 118 when the measurement is requested in the cross mixing test. As illustrated in FIG. 4, the cross mixing test measurement request screen (operation screen) has a region for displaying a type of the specimen, that is, any one of a general specimen, an urgent specimen, and control. FIG. 4 illustrates that the cross mixing measurement of the general specimen is requested. In addition, the cross mixing measurement request screen (operation screen) has a test item selection/designation region 127. An operator can designate an item for performing the cross mixing test from the test item selection/designation region 127 through the operation screen. The example illustrated in FIG. 4 shows a state where an item APTT is selected and designated. In addition, the operation screen has a region in which a normal blood plasma ratio can be selectively designated. The example illustrated in FIG. 4 shows a state where seven conditions of the normal blood plasma ratios of 0%, 10%, 20%, 50%, 80%, 90%, and 100% are all set. Here, the normal blood plasma ratios to be set are not limited to the seven conditions illustrated in FIG. 4. For example, it is possible to select three or more conditions including 0% and 100%. That is, as long as the subject blood plasma alone, the normal blood plasma alone, and the mixed blood plasma of at least one mixing ratio are set, other mixing ratios can be optionally set.

As illustrated in FIG. 4, if the measurement item and the normal blood plasma ratio are set, the analysis operation control unit 120a calculates the normal blood plasma amount and the subject blood plasma amount which are required for measurement, and determines each of the normal blood plasma amount and the subject blood plasma amount which are different depending on the conditions, thereby controlling the operation of the specimen dispensing mechanism 101. In this case, as illustrated in FIG. 5, the operator is informed by displaying the required normal blood plasma amount and the required subject blood plasma amount on the display unit 118c. Since the operator can recognize the required blood plasma amount, there is an advantageous effect in that the burden of the operator calculating the required amount is reduced and the operator can be prevented from lacking blood plasma amount during the preparation. Here, in FIG. 5, the operator designates the installation position of the normal blood plasma, the subject blood plasma, and the vacant specimen container, but the device may be controlled so as to designate the installation position. In addition, FIG. 5 illustrates a state where "100" is set as the installation position of the normal blood plasma, "101" is set as the installation position of the subject blood plasma, and "102" is set as a start position of the vacant specimen container. Here, each position represents a position of the specimen container 103 in the specimen disc 102. It is not necessarily specified by only numbers. For example, a combination of alphabets and numbers may specify the position of the specimen container 103.

In addition, in a case where the request is received from the network system using the host computer, the analysis can be performed without setting the measurement item or the measurement condition.

In a state illustrated in FIG. 5, if a "start" button is pressed (Step S102), the normal blood plasma amount, the subject blood plasma amount, and the presence of the vacant specimen container are confirmed (Step S103). Here, the vacant specimen container is a disposable and closable container having an individual identification medium. The individual identification medium is used for identifying the specimen. For example, a barcode or RFID is used. In the individual identification medium of the subject specimen, in addition to a specimen ID for identifying the specimen, measurement request information is included. The individual identification medium affixed to the vacant specimen container is used for managing the mixed blood plasma after an optional number is assigned and the normal blood plasma and the subject blood plasma are mixed. In order to confirm the normal blood plasma amount, the subject blood plasma amount, the presence of the vacant specimen container, a liquid level detection function of the specimen dispensing mechanism 101 is used. That is, the specimen dispensing probe 101a disposed in the distal end of the specimen dispensing mechanism 101 detects a liquid level by utilizing a change in electric characteristics such as electrostatic capacity and a resistance value which vary when an object comes into contact with or comes close to the liquid level. Alternatively, a configuration may be adopted in which an image is captured using an imaging function (sensor such as CCD, CMOS, and PMT) by a small camera so as to calculate a liquid amount from the height of the liquid level. In the following description, a case of using the liquid level detection function of the specimen dispensing mechanism 101 and using the barcode as the individual identification medium will be described as an example.

When the subject specimen and the vacant specimen container which are installed at the designated position in FIG. 5 pass in front of the reading unit 125 by the rotation of the specimen disc 102 rotating clockwise and counterclockwise, the barcode serving as the individual identification medium of the subject specimen is read. The request item for the subject specimen specified by the read barcode is verified, and the normal blood plasma ratio or the original subject specimen information prepared in the installed vacant specimen container is verified with an ID of each mixed blood plasma. Subsequently, as illustrated in FIG. 6, in the specimen container 103 in the specimen disc 102, the specimen container 103*a* filled with the normal blood plasma is moved to a dispensing position of the specimen dispensing mechanism 101, and the normal blood plasma amount is confirmed using the liquid level detection function of the specimen dispensing probe 101*a*. In a similar manner, the specimen container 103*b* filled with the subject blood plasma is moved to the dispensing position, and the subject blood plasma amount is confirmed using the liquid level detection function of the specimen dispensing probe 101*a* (FIG. 7). Furthermore, as for the vacant specimen container, in a case where the liquid level detection function of the specimen dispensing probe 101*a* detects that there is no contact with the liquid surface and the specimen container comes into contact with the bottom (abnormal descent detection), it is recognized that the installed specimen container is vacant.

Referring back to FIG. 3, in Step S104, as a result of the container installation check, the normal blood plasma amount and the subject blood plasma amount are less than the required amount, or the required number of vacant specimen containers is not installed at the predetermined position. In this case, the mixed blood plasma preparation is canceled, and a system alarm is displayed (Step S105). In this manner, the blood plasma is further dispensed to a place where the blood plasma is insufficient during the measurement or a place where the vacant specimen container is not installed, that is, the specimen container where the specimen (the normal blood plasma, the subject blood plasma, or the mixed blood plasma) is previously dispensed. Accordingly, it is possible to avoid the risk of contaminating the specimen disc 102.

In Step S104, in a case where the normal blood plasma amount and the subject blood plasma amount are prepared more than necessary and it can be confirmed that the required number of vacant specimen containers is installed, the normal blood plasma starts to be dispensed to the vacant specimen container (Step S106).

Here, a dispensing operation of the normal blood plasma will be described. Rotation of the specimen disc 102 rotating clockwise and counterclockwise causes the specimen container 103*a* filled with the normal blood plasma to move to the dispensing position, and causes the specimen dispensing mechanism 101 to aspirate the normal blood plasma (FIG. 6). The example illustrated in FIG. 6 shows a case where the specimen disc 102 is rotated counterclockwise in a stepwise manner. A moving distance in each step is equivalent to a pitch of the two specimen containers 103 arranged adjacent to each other. In this manner, the reading unit 125 reads the barcode affixed to the specimen container 103 as described above so as to identify the specimen ID. Thereafter, the specimen container 103 is moved along the rotation direction of the specimen disc 102, and is positioned (at the specimen dispensing position) immediately below the specimen dispensing mechanism 101 located in front of the reading unit 125. That is, each of the specimen containers 103 is always positioned at the dispensing position after the specimen ID is identified by the reading unit 125.

Next, the specimen container 103 positioned at the dispensing position by the stepwise rotation of the specimen disc 102 is the specimen container 103*b* filled with the subject blood plasma (FIG. 7). Accordingly, the specimen dispensing mechanism 101 does not discharge the normal blood plasma aspirated by the specimen dispensing probe 101*a*. Subsequently, the specimen container positioned at the dispensing position is the vacant specimen container 103*c*, and discharges the normal blood plasma aspirated into the specimen dispensing probe 101*a* (FIG. 8). This operation is repeatedly performed, and the normal blood plasma is dispensed to vacant specimen containers 103*d* to 103*i*. If the normal blood plasma is completely dispensed (Step S107), the subject blood plasma is subsequently dispensed (Step S108).

In the dispensing operation of the subject blood plasma in Step S108, first, the specimen container 103*b* filled with the subject blood plasma is positioned at the dispensing position by the rotation of the specimen disc 102, and the subject blood plasma is aspirated by the specimen dispensing probe 101*a* of the specimen dispensing mechanism 101 (FIG. 7). Subsequently, the specimen container positioned at the dispensing position by the rotation of the specimen disc 102 is the specimen container 103*c* from which the normal blood plasma is discharged in Step S106. The specimen dispensing probe 101*a* discharges the aspirated subject blood plasma to the specimen container 103*c* (FIG. 8). In the same procedure, the subject blood plasma is dispensed to the specimen containers 103*d* to 103*i* by the specimen dispensing probe 101*a*. This operation is repeatedly performed until the subject blood plasma is all dispensed (Step S109).

In Step S106 and Step S108, the discharge amount of the normal blood plasma and the subject blood plasma which are discharged to each of the specimen containers 103*c* to 103*i* by the specimen dispensing probe 101*a* configuring the specimen dispensing mechanism 101 corresponds to the normal blood plasma ratio set by the operation screen illustrated in FIG. 4, for example.

Referring back to FIG. 3, in Step S110, as illustrated in FIG. 9, the mixed blood plasma of the normal blood plasma and the subject blood plasma which are dispensed into the specimen container 103*c* positioned immediately below a stirring mechanism 126 is stirred by the stirring mechanism 126. Here, for example, as illustrated in FIG. 9, the stirring mechanism 126 performs the stirring operation in such a way that a stirring blade or a spatula-shaped rod disposed in the distal end is rotated while being dipped into the mixed blood plasma inside the specimen container 103*c*. The stirring mechanism 126 is not limited to a system which rotates the stirring blade or the spatula-shaped rod. For example, a configuration may be adopted in which the mixed blood plasma in the specimen container is irradiated with ultrasonic waves and stirred. Alternatively, a configuration may be adopted in which the specimen disc 102 is rotated in the forward and reverse directions (clockwise and counterclockwise). Alternatively, a configuration may be adopted in which the mixed blood plasma is stirred using discharge pressure when the normal blood plasma or the subject blood plasma is discharged from the specimen dispensing probe 101*a* to the specimen container 103, that is, discharge pressure of the specimen syringe pump 105.

In this way, in the automatic analysis device 100 according to the present embodiment, the mixed blood plasma having various normal blood plasma ratios set by the above-described operation screen illustrated in FIG. 4 can be automatically prepared by the specimen dispensing mechanism 101 and the stirring mechanism 126.

In FIG. 3, a configuration is adopted in which the subject blood plasma is dispensed (Step S108) after the normal blood plasma is dispensed (Step S106). However, without being limited thereto, a configuration may be adopted in which the mixed blood plasma is prepared by dispensing the normal blood plasma after the subject blood plasma is dispensed. In addition, from a viewpoint of preventing the contamination of the normal blood plasma and the subject blood plasma, the normal blood plasma and the subject blood plasma are independently dispensed. However, the embodiment is not limited thereto. For example, in a case where the specimen dispensing mechanism 101 is sufficiently cleaned and there is no worry about the contamination, it is possible to produce (prepare) the mixed blood plasma one by one. In this case, after the required amount of the normal blood plasma is dispensed to the vacant specimen container 103c, the required amount of the subject blood plasma is dispensed. After the mixed blood plasma of the specimen container 103c is produced, the mixed blood plasma is sequentially produced for each vacant specimen container so as to produce the mixed blood plasma of the vacant specimen container 103d.

In addition, when two types of specimen are dispensed, when the processes are completed until Step S109 in FIG. 3, a screen indicating the preparation completion is displayed on the display unit 118c. The specimen container containing the prepared specimen is closed and stirred by the operator. In this manner, the specimen container may be installed again on the specimen disc 102. In this case, since it is not necessary to provide the specimen stirring mechanism 126, the device can decrease in size.

After the specimen is prepared, the analysis is performed using seven mixed blood plasmas prepared on the specimen containers 103c to 103i. In this way, the measurement to be carried out immediately after the specimen is prepared is defined as an immediate-type measurement. In Step S111 of FIG. 3, the barcode affixed to the specimen containers 103c to 103i containing the mixed blood plasma having seven mutually different normal blood plasma ratios is read by the reading unit 125. The reading unit 125 specifies each normal blood plasma ratio of the normal blood plasma alone, the subject blood plasma alone, and five mixing ratios, that is, 10, 20, 50, 80, and 90% of the mixed blood plasma ratio. Thereafter, the process proceeds to Step S112. In Step S112, the specimen contained in each of the specimen containers 103c to 103i is dispensed to the different reaction containers 104 to be contained inside the reaction container stock unit 111 by the specimen dispensing mechanism 101. Thereafter, each reaction container 104 is moved to the detecting unit 113 by the reaction container transport mechanism 112, the reaction container 104 is set in the reaction container installation unit 114 as described above, and the measurement signal indicating the intensity of the scattered light and/or the transmitted light is detected. Here, the specimen container of the seven prepared specimens has a function which can verify the measurement result by recognizing the normal blood plasma ratio verified in Step S103 and the subject specimen ID.

Incidentally, this cross mixing test is different from that of the ordinary analysis as follows. A plurality of (in this case, seven) APTT coagulation times are calculated for one subject specimen, and one graph is prepared so as to be used for the diagnosis. For example, in order to display the result after the immediate-type measurement is completed, the operation unit 118c displays a graph obtained by plotting that the normal blood plasma ratio of each mixed blood plasma is set as the horizontal axis as illustrated by a solid line (a) in FIG. 10 and the APTT coagulation time is set as the vertical axis (Step S113). The verification of the measurement result obtained by the individual identification medium and the automatic graph preparation function can prevent the operator from erroneously inputting the measurement result, and can provide reliable results. In this case, it is preferable that the result is printed out from the printer 123 via the interface 122.

In a case where delayed-type measurement is subsequently performed after the immediate-type measurement (Step S114), the container of the mixed blood plasma (remaining specimen) after the immediate-type measurement is closed, and is incubated at 37° C. for a prescribed time in the incubator 124. However, in a case of the device having no incubator 124, the incubation is performed outside the device. Here, a case will be described where the incubation is performed outside the device without providing the incubator 124 for the device in order to save space and cost of the device. The device counts an incubation time starting from the measurement completion time. In this case, the operator can recognize the completion time of the incubation from the operation screen by presetting the incubation time. In addition, it is preferable to output a display informing the completion of the incubation, when the incubation completion is in time (Step S115). In this manner, the operator can recognize a situation of the specimen during incubation, and can perform the measurement without forgetting the situation. The operator opens the specimen container of the mixed blood plasma whose incubation is completed, installs the specimen container on the specimen disc 102, and presses the measurement start button. If the measurement start button is pressed (Step S116), the mixed blood plasma ID set at the position designated on the operation screen illustrated in FIG. 5 is read by the rotation of the specimen disc 102. The normal blood plasma ratio verified in Step S103 and the subject specimen ID are recognized. The request item is verified (Step S117), and the delayed-type measurement is performed (Step S118). If the measurement is completed, a delayed-type graph illustrated by a solid line (b) in FIG. 10 is prepared (Step S119), and is verified with the immediate-type result (Step S120). In this case, as illustrated in FIG. 2, the immediate-type graph and the delayed-type graph may be combined into one, or may be displayed by being divided into two mutually different graphs.

As described above, according to the present embodiment, the mixed blood plasma production, the immediate-type/delayed-type analysis, and the immediate-type/delayed-type result verification are automatically performed. Accordingly, the measurement result does not vary depending on the skill level of the operator, and a human mistake is eliminated in handling the specimen. Therefore, it is possible to further improve reliability.

In addition, the burden of the operator is reduced, and thus, it is possible to quickly obtain the result.

Furthermore, it is possible to realize the automatic analysis device and the automatic analysis method which enable automated preparation of the mixed blood plasma obtained by mixing the subject blood plasma and the normal blood plasma at a prescribed mixing ratio.

Example 2

FIG. 11 is an overall schematic configuration diagram of an automatic analysis device of Example 2 according to another embodiment of the present invention. In the present embodiment, the automatic analysis device includes a specimen rack 201, a specimen rack supply unit 202, a specimen rack accommodation unit 203, a transport line 204 which transports the specimen rack 201 to an analysis unit 210, a return line 205, a rack standby unit 206, a standby unit handling mechanism 207, a rack returning mechanism 208, a first reading unit (transport line) 209, and the analysis unit 210. That is, as a mechanism for mounting the specimen container 103, the specimen container 103 is mounted on the specimen rack 201, and various transport mechanisms for transporting the specimen rack 201 are provided. This point is different from that according to Example 1. The other points are similar to those according to Example 1. The same reference numerals will be given to configuration elements the same as those according to Example 1, and description thereof will be omitted below.

As illustrated in FIG. 11, a configuration is adopted in which a plurality of analysis units 210 can be connected to each other along the transport line 204. However, according to the present embodiment, a configuration is adopted which includes at least one analysis unit for carrying out a coagulation test. The basic configuration of the analysis unit 210 and the basic analysis flow for carrying out the coagulation test are generally similar to those according to Example 1. However, since the specimen is supplied via the transport line 204, the present embodiment does not have the specimen disc 102.

Hereinafter, a supply method of the specimen, which is greatly different from that according to Example 1, will be described in detail.

In the automatic analysis device according to the present embodiment, a transport system of the analysis unit 210 disposed along the transport line 204 includes a second reading unit (analysis unit) 211 for verifying analysis request information relating to the specimen, a first rack handling mechanism 212 which receives the specimen rack 201 from the transport line 204, a dispensing line 213 which is provided with a function to put the specimen rack 201 on standby until the dispensing starts, and which dispenses the specimen inside the specimen container of the specimen rack 201, an evacuation area 214 for evacuating the specimen rack 201 when the mixed blood plasma is prepared for the cross mixing, and a second rack handling mechanism 215 which transports the specimen dispensed specimen rack 201 to the return line 205.

First, a specimen supply flow in general analysis, that is, when performing analysis with a calibrator, a control, or a general specimen, that is, a transportation procedure of the specimen racks will be described with reference to FIG. 12.

If an analysis request is received via the operation unit 118, the specimen racks 201 arrayed in the specimen rack supply unit 202 are transferred to the transport line 204 as illustrated by an arrow (a) in FIG. 12. Thereafter, the individual identification medium (for example, a barcode) affixed to the specimen container accommodated in the specimen rack 201 and the specimen rack 201 is read by the first reading unit (transport line) 209. The specimen rack number and the specimen container number are recognized (arrow (b) in FIG. 12). Thereafter, if the specimen read by the first reading unit (transport line) 209 is accommodated in the specimen rack standby unit 206, and stands by the analysis, if the specimen rack 201 is present in the dispensing line 213 (arrow (c) in FIG. 12). The specimen rack 201 brought into a standby state in a stage where the specimens of the dispensing line 213 are completely dispensed is sent to the analysis unit 210. The specimen rack number and the specimen container number are recognized by the second reading unit (analysis unit) 211 ((d) in FIG. 12). Subsequently, the specimen rack 201 is drawn into the dispensing line 213 by the first rack handling mechanism 212 ((e) in FIG. 12), and the specimen is dispensed by the specimen dispensing mechanism 101. In this case, if the specimen rack 201 is not present in the dispensing line 213, the specimen is directly transported to the dispensing line 213 without being accommodated in the specimen rack standby unit 206.

The specimen rack 201 accommodating the specimen which is completely dispensed by the specimen dispensing mechanism 101 is transported to the return line 205 via the second rack handling mechanism 215 ((f) in FIG. 12), and is transported to the specimen rack standby unit 206 via the standby unit handling mechanism 207 ((g) in FIG. 12). Here, the specimen rack 201 stands by the measurement result. In a case where it is determined that there is no retest, the specimen rack 201 is transferred to the return line 205 via the standby unit handling mechanism 207 ((h) in FIG. 12), and is transported to the specimen rack accommodation unit 203 ((i) in FIG. 12).

FIG. 13 illustrates a specimen supply flow in preparing the specimen of the cross mixing test, that is, a transportation procedure of the specimen racks.

If the analysis request is received from the operation unit 118, the specimen racks 201 arrayed in the specimen rack supply unit 202 is transferred to the transport line 204 (arrow (a) in FIG. 13). Thereafter, the individual identification medium (for example, a barcode) affixed to the specimen container accommodated in specimen rack 201 and the specimen rack 201 is read by the first reading unit (transport line) 209. The specimen rack number and the specimen container number are recognized ((b) in FIG. 13). In a case where the request for the cross mixing test is confirmed by the first reading unit (transport line) 209, the specimen racks 201 accommodating the normal blood plasma, the subject blood plasma, and the vacant specimen container are all verified, and stand by the analysis after being accommodated in the rack standby unit 206 until there is no more analyzing specimen in the dispensing line 213 (arrow (c) in FIG. 13). In this case, even if the subject blood plasma, the normal blood plasma, and the vacant specimen container are all accommodated in the same specimen rack, all of these may be accommodated over two or more specimen racks.

When the dispensing line 213 has no analyzing specimen and the specimen rack 201 accommodating the subject blood plasma, the normal blood plasma, and the vacant specimen container which are analysis targets can be confirmed, the specimen rack accommodating the subject blood plasma serving as the analysis target, and the specimen rack accommodating the vacant specimen container are transported to the analysis unit 210 in this order. Then, the specimen rack number and the specimen container number are recognized by the second reading unit (analysis unit) 211 ((d) in FIG. 13). Subsequently, the specimen rack is sent to the dispensing line 213 via the second rack handling mechanism 215 ((e) in FIG. 13). Similarly to Example 1 described above, the liquid level detection function and the abnormal descent detection function of the specimen dispensing mechanism 101 are used so as to confirm whether the specimen container 103 is filled with the required amount of the subject blood plasma and the normal blood plasma and whether the specimen container 103 required for preparing the mixed blood plasma is vacant.

Here, in a case where the subject blood plasma amount, the normal blood plasma amount, and the vacant specimen container are not correctly installed, the specimen container 103 is once returned to the transport line 204 via the first rack handling mechanism 212. Thereafter, the specimen container 103 is transported to the return line 205 via the second rack handling mechanism 215. If the specimen container 103 returns to the specimen rack accommodation unit 203, a system alarm is output, and the specimen preparation is canceled.

On the other hand, the specimen rack 201, in which it is confirmed that the subject blood plasma amount, the normal blood plasma amount, and the vacant specimen container are correctly installed, returns once to the transport line 204 via the first rack handling mechanism 212, and is transported again to the dispensing line 213 via the second rack handling mechanism 215. The specimen rack 201 aspirates the subject blood plasma of the transported specimen rack 201, and subsequently discharges the subject blood plasma to the vacant specimen container. In this case, in a case where the vacant specimen container is accommodated in another specimen rack, the specimen rack is loaded in the evacuation area 214 disposed on the dispensing line 213, and is discharged to the vacant specimen container by the arc-shaped rotation operation inside the horizontal plane of the specimen dispensing mechanism 101 (FIG. 14). The same operation is repeatedly performed, and the subject blood plasma and the normal blood plasma are dispensed, thereby producing the mixed blood plasma. In this case, it is desirable to adopt a configuration in which the stirring mechanism 126 described in Example 1 is disposed to be accessible to the dispensing line 213 so that the mixed blood plasma can be mixed.

The specimen rack accommodating the prepared specimen returns to the transport line 204 via the first rack handling mechanism 212, and is sent to the return line 205 via the second rack handling mechanism. 215 ((g) in FIG. 13). Thereafter, the specimen rack 201 accommodating the prepared specimen is drawn into the specimen rack standby unit 206 via the standby unit handling mechanism 207 ((h) in FIG. 13), and stands by the analysis. Here, as illustrated in FIG. 11, in a case of a structure where the analysis unit 210 does not include the stirring mechanism 126, the specimen rack 201 is sent to the return line 205 via the second rack handling mechanism 215 ((g) in FIG. 13), and returns to the specimen rack accommodation unit 203 ((g) in FIG. 13). The operator collects the prepared specimen from the returned specimen rack, installs the specimen rack 201 in the rack supply unit 202 again after stirring, and performs the analysis of any desired item (for example, APTT) (immediate-type measurement). Since the analysis method is the same as that in Example 1, description thereof will be omitted.

The analyzed specimen is sent to the return line 205 via the second rack handling mechanism 215 ((g) in FIG. 13), and returns to the specimen rack accommodation unit 203 ((g) in FIG. 13). The operator collects the specimen returning to the specimen rack accommodation unit 203, performs the incubation at 37° C. for a prescribed time, installs the specimen again in the specimen rack supply unit 202, and performs the delayed-type measurement.

According to the present embodiment, in addition to the advantageous effect of Example 1, the immediate-type measurement and the delayed-type measurement can be easily performed by controlling the transporting direction of the specimen rack.

Example 3

FIG. 15 is a flowchart illustrating a process flow of an automatic analysis device in Example 3 according to another aspect of the present invention. In the present embodiment, as a configuration of the automatic analysis device itself, any configuration of Example 1 or Example 2 described above may be employed. Instead of preparing a measurement target specimen (preparing the mixed blood plasma) inside the specimen container, the normal blood plasma and the subject blood plasma are directly dispensed into the reaction container so as to prepare the measurement target specimen. This point is different from that according to Example 1 and Example 2. That is, in the present embodiment, the measurement is performed by adding the reagent after the normal blood plasma and the subject blood plasma are directly dispensed into the reaction container. Accordingly, a loss of the specimens is minimized compared to the method as in Example 1 and Example 2 where the normal blood plasma and the subject blood plasma are mixed in a separate container, and in which after the mixed blood plasma is produced, the mixed blood plasma is dispensed again into the reaction container during the measurement.

As illustrated in FIG. 15, first, the automatic analysis device receives a request for the cross mixing test via the operation unit 118 (Step S301). Thereafter, similarly to Example 1 and Example 2 described above, the process until the pressed "start" button illustrated in FIG. 5 is recognized (Step S302) is the same as that according to Example 1.

Figure 16:
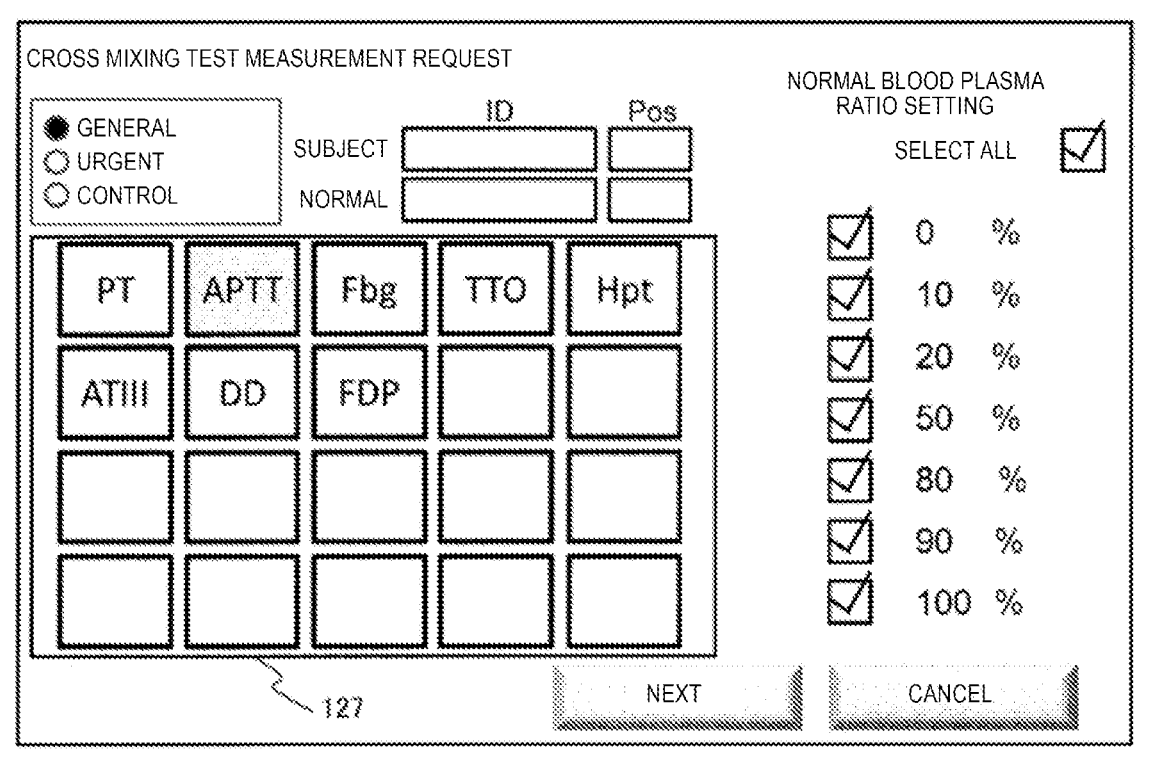

As illustrated in FIG. 16, on the cross mixing measurement request screen according to the present embodiment, the operator sets the normal blood plasma ratio similarly to Example 1, selects and designates the analysis item by using the test item selection/designation region 127. Here, as illustrated in FIG. 16, in this embodiment, in addition to the subject ID, a region to which the normal blood plasma ID and the position of the subject blood plasma/normal blood plasma can be input is disposed on the operation screen. If the "start" button is pressed, in a case where the individual identification medium such as the barcode of the subject blood plasma/normal blood plasma is affixed, the specimen ID of the subject blood plasma/normal blood plasma passing in front of the reading unit 125 is recognized by the rotation of the specimen disc 102. In a case of failing to read the specimen ID or in a case where the individual identification medium is not affixed, the specimen ID can be recognized by manually inputting the specimen ID to the column of the specimen ID and the position of the subject blood plasma/normal blood plasma on the operation screen in FIG. 16. In addition, in a case of receiving the requests from the network system using the host computer, the analysis can be performed without setting the measurement item or the measurement condition.

If the start button is pressed (Step S302), the specimen dispensing mechanism 101 aspirates the normal blood plasma installed on the specimen disc 102, and dispenses the normal blood plasma to the reaction container 104 (Step S303). Subsequently, the subject blood plasma is aspirated and dispensed to the reaction container 104 (Step S304). Here, a dispensing procedure in the order of the normal blood plasma and the subject blood plasma has been described, but the order of Steps S303 and S304 may be reversed. In addition, after the normal blood plasma is aspirated, the normal blood plasma may not be soon discharged to the reaction container 104. Alternatively, the subject blood plasma may be aspirated and discharged to the reaction container 104 together with the normal blood plasma.

If the measurement is the immediate-type measurement (Step S305), the reaction container transport mechanism 112 grips the reaction container, and moves to the detecting unit 113 (Step S306). Thereafter, the reagent dispensing (Step S307) and the detection (Step S308) are performed by the reagent dispensing mechanism 106. The processes are repeatedly performed until all of the specimens having the normal blood plasma ratio set on the operation screen illustrated in FIG. 16 are completely measured (Step S309).

A graph of the immediate-type measurement result is prepared after the measurement is completed (Step S310).

In addition, in a case where the measurement of the reaction container is not the immediate-type measurement in Step S305, that is, in a case of the delayed-type measurement, the reaction container 104 is moved to the incubator 124 (Step S311), and a heating start time is stored. All mixed blood plasmas (Step S312) having the normal blood plasma ratio set on the operation screen illustrated in FIG. 16 are repeatedly prepared, and all mixed blood plasmas are incubated. In a stage of a heating completion time (Step S313), the reaction container transport mechanism 112 grips the reaction container 104, and moves the reaction container 104 to the detecting unit 113 (Step S314). In the present embodiment, since the incubation time can be controlled inside the automatic analysis device, it is possible to reduce the risk of outputting erroneous results caused by an insufficient or excessive incubation time. Here, the time is displayed on the operation screen so as to recognize that the incubation of the cross mixing test is in progress. It is more preferable to provide a function which can flexibly set the incubation time. Thereafter, the reagent dispensing (Step S315) and the detection (Step S316) are performed by the reagent dispensing mechanism 106. The processes are repeatedly performed until all of the prepared specimens are completely measured (Step S317). A graph of the delayed-type measurement result is prepared after the measurement is completed (Step S318).

Next, in Step S319, the graph of the immediate-type measurement result obtained in Step S310 and the graph of the delayed-type measurement result obtained in Step S318 are verified so as to be set as a final result (Step S319).

As described above, according to the present embodiment, the normal blood plasma and the subject blood plasma are directly dispensed to the reaction container 104, and preparation, incubation, measurement and output of measurement results for the mixed blood plasma are fully automatically performed. In this manner, it is possible to provide highly reliable results which do not depend on an operator's skill level. In addition, the burden of the subject can be reduced by minimizing the amount of the specimen used for the preparation.

In addition, the present embodiment adopts a configuration in which it is possible to directly input the position of the specimen container filled with the normal blood plasma and the subject blood plasma. Therefore, the present embodiment is applicable to facilities operated without using the specimen ID management function.

Example 4

FIG. 17 illustrates a process flow of an automatic analysis device in Example 4 according to another aspect of the present invention. In Example 1 to Example 3, the method of carrying out the cross mixing test has been described. However, the automatic analysis device does not carry out only the cross mixing test, but is usually used in understanding pathology conditions of the coagulation fibrinolysis system, diagnosing disseminated intravascular coagulation syndrome (DIC), and confirming a thrombus treatment effect. That is, when the delayed-type analysis is performed on the mixed blood plasma for the cross mixing test which completes the incubation, if a usual analysis request is made at the same time, the mixed blood plasma for the cross mixing test cannot be always immediately analyzed. Therefore, the automatic analysis device according to the present embodiment has a function which can select a priority of the test for each specimen classification. This point is different from that according to Example 1 to Example 3.

In order to respond to the promptness required when a blood coagulation ability test is carried out before surgery in a clinical test and when a test result is reported to an outpatient on the same day, the automatic analysis device described in the present embodiment has a function which can perform analysis by giving a higher priority to a promptness-requiring specimen than a usual specimen. Here, the promptness-requiring specimens are collectively defined as an urgent specimen, and the analysis can be performed with the higher priority over the general specimen. On the other hand, in the mixed blood plasma for the cross mixing test, the incubation time is controlled. Accordingly, there is a demand for an immediate measurement in a case where the incubation is completed for a prescribed time. Therefore, a process will be described with reference to FIG. 17. In the process, in order to satisfy the needs of the operator, priorities can be selected for each specimen classification, and the measurement order is determined in accordance with the priorities. In FIG. 17, a case where the priorities are set to "the urgent specimen measurement>the delayed-type cross mixing test>the general specimen measurement" will be described as an example. However, the priority settings are not limited to this form.

When the incubation of the mixed blood plasma prepared for the delayed-type cross mixing test is completed (Step S401), in a case where the device is not in a standby state, the processes follow the following flow (Step S402). It is determined whether or not there is a request for the urgent specimen in scheduled items (Step S403). In a case where there is no request for the urgent specimen, the process proceeds to Step S406. The items are rescheduled so as to carry out the delayed-type cross mixing test with the higher priority over the general specimen (Step S406). However, in a case where the analysis of the urgent specimen is requested, the analysis is performed in the order of the urgent specimen, the cross mixing test, and the general specimen. Accordingly, during the analysis of the urgent specimen, the mixed blood plasma for the cross mixing test is once brought into a standby state in the incubator 124 (Step S404). When the urgent specimen is completely analyzed (Step S405), the items are rescheduled so as to carry out the delayed-type cross mixing test with the higher priority over the request of the general specimen (Step S406). Here, when the incubation of the mixed blood plasma prepared for the delayed-type cross mixing test is completed (Step S401), if the device is in the standby state, the above-described scheduling is unnecessary. As described below, the analysis of the cross mixing test starts.

First, the mixed blood plasma prepared for the delayed-type cross mixing test is moved from the incubator 124 to the detecting unit 113 (Step S407). Subsequently, a reagent is dispensed to the prepared mixed blood plasma (Step S408), and the detection is performed (Step S409). The processes from Step S407 to Step S409 are repeatedly performed until all of the mixed blood plasmas prepared for the delayed-type cross mixing test are completely analyzed. If the mixed blood plasmas are completely analyzed (Step S410), the result of the cross mixing test is calculated and output (Step S411).

Thereafter, in a case where the request for the general specimen still remains (Step S412), the general specimen is analyzed (Step S413). If the general specimen is completely analyzed (Step S414), the automatic analysis device is brought into a standby state (Step S415).

FIG. 18 is a timing chart illustrating an operation of the automatic analysis device illustrated in FIG. 17. As illustrated in FIG. 18, in a case where the automatic analysis device itself in the standby state receives a measurement request for the general specimen, the automatic analysis device is brought into an operation state in order to measure the general specimen. In this case, if a measurement request for the urgent specimen is received, the priority settings are made in advance as described above. The highest priority is given to the urgent specimen measurement process, the subsequent priority is given to the delayed-type measurement of the specimen (mixed blood plasma) for the cross mixing test, and the lowest priority is given to the general specimen measurement. Therefore, the highest priority is given to the urgent specimen processing. After the urgent specimen processing is completed, if the incubation time of the mixed blood plasma for the cross mixing test is completed again while the general specimen processing starts, the general specimen processing is once interrupted, and the delayed-type measurement starts. In a case where the measurement request for the urgent specimen is received while the delayed-type measurement is performed, even in a case where the highest priority is set for the urgent specimen processing, the urgent specimen processing is brought into a standby state until the delayed-type measurement is completed. After the cross mixing test is completed, the urgent specimen is analyzed.

As described above, according to the present embodiment, in addition to the advantageous effect according to Example 1 and Example 2, the operator presets a priority for each specimen, such as the general specimen and interruption processing for the urgent specimen. In this manner, based on the set priority, the automatic analysis device can perform the analysis. Therefore, a human mistake can be minimized in erroneously handling the specimen, and the automatic analysis device can be efficiently operated.

Example 5

FIG. 19 is a flowchart illustrating a process flow of an automatic analysis device in Example 5 according to another aspect of the present invention. The present embodiment is different from Example 1 to Example 4 described above in that the reagent is managed based on the number of mixed blood plasma specimens. The configurations other than the reagent management method are the same as those according to Example 1 to Example 4, and thus, description thereof will be omitted below.

For example, in the cross mixing test, seven measurement values are treated as one set of results. Accordingly, it is necessary to secure the reagent in the same lot (preferably, the same bottle) for one set of measurements. In particular, in a case where the measurement item is APTT, the calibration is not performed. Consequently, the measurement results tend to vary in the reagent in the different lot. In addition, even in the same lot, the reagent inside the reagent container (reagent bottle) which is stored in the device for awhile and the reagent in a newly opened reagent container (reagent bottle) are likely to vary. Therefore, in this automatic analysis device according to the present embodiment, in a case where the analysis request for the cross mixing test is confirmed, it is important to secure the reagent which can be used in performing one set of measurements at least once. As illustrated in FIG. 19, if the immediate-type analysis request is received (Step S501), the control unit 120 confirms the required number of tests (the number of prepared mixed blood plasmas) and the remaining amount of the reagent. That is, it is determined whether or not a relationship satisfies "the number of mixed blood plasma specimens the number of reagent remaining tests" (Step S502). In a case where the determination result in Step S502 is "NO", that is, in a case where the number of mixed blood plasma specimens exceeds the number of reagent remaining tests, the process proceeds to Step S504, and an alarm is displayed on the display unit 118c. In addition, in a case where the determination result in Step S502 shows that the number of mixed blood plasma specimens is equal to or smaller than the number of reagent remaining tests, the process proceeds to Step S503, and cross mixing test is carried out (analysis is performed).

In addition, in a case where a plurality of reagent bottles having the same item are installed, the control unit 120 controls the bottles so as not to collectively analyze at least one set of measurements. For example, when the number of remaining tests of a bottle 1 is "3 tests" and the number of remaining tests of a bottle 2 is "100 tests", in a case where the cross mixing test is requested at 7 points (7 conditions), "the number of mixed blood plasma specimens (seven) the number of reagent remaining tests of the bottle 1" is satisfied. Accordingly, the analysis in the bottle 1 is cancelled, and the number of remaining tests in the bottle 2 is verified. In a case of the bottle 2, "the number of mixed blood plasma specimens (seven) the number of reagent remaining tests of the bottle 2" is satisfied. Accordingly, the cross mixing test (analysis) is carried out. In addition, in a case where there is no reagent bottle which can be analyzed, a system alarm is output, and the analysis start is canceled (Step S504).

According to the present embodiment, it is possible to perform analysis using the reagent in the same bottle without causing the reagent shortage in the middle of the analysis with regard to one set of cross mixing tests. In addition, this configuration can provide highly reliable results.

Example 6

FIG. 20 is a flowchart illustrating a process flow of an automatic analysis device in Example 6 according to another aspect of the present invention. In the present embodiment, the method of preparing the mixed blood plasma is different from the above-mentioned methods according to Example 1 to Example 5. In addition, the configuration of the automatic analysis device and the flow of the general coagulation test are the same as those according to Example 1 or Example 2, and thus, repeated description will be omitted below. In addition, with regard to the method of preparing the specimen, points the same as those according to Example 1 will be briefly described as much as possible.

As illustrated in FIG. 5, Example 1 and Example 2 described above adopt a configuration in which the required normal blood plasma amount and the required subject blood plasma amount are displayed on the display unit 118c and the operator is informed of the displayed information so as to avoid the risks of the specimen shortage during the preparation. However, in a case where the normal blood plasma amount and/or the subject blood plasma amount are insufficient due to a mistake of the operator, the specimen shortage occurs during the preparation, and the prepared specimen become useless. Therefore, according to the automatic analysis device of the present embodiment, even in a case where the normal blood plasma and/or the subject blood plasma to be prepared are insufficient as described above, the specimen is no longer useless, thereby enabling the measurement to be effectively performed.

As illustrated in FIG. 20, if the automatic analysis device receives the request for the cross mixing test (Step S601) and the measurement item and the normal blood plasma ratio are set, the analysis operation control unit 120a performs the following processes. That is, the analysis operation control unit 120a calculates the normal blood plasma amount and the subject blood plasma amount which are required for the measurement, determines each of the normal blood plasma amount and the subject blood plasma amount which vary depending on each condition, and controls the operation of the specimen dispensing mechanism 101.

Subsequently, if the "start" button on the operation screen illustrated in FIG. 5 is pressed, the analysis operation control unit 120a recognizes that the "start" button is pressed (Step S602). Subsequently, the presence or absence of the vacant specimen container is confirmed (Step S603). The method of confirming the presence or absence of the vacant specimen container is the same as that in the process (Example 1) of Step S103 in FIG. 3.

In Step S604, it is determined whether or not the number of the vacant specimen containers obtained by performing Step S603 is N (N is a natural number) or more. For example, in this case, N is set to seven, which is the number of the vacant specimen containers corresponding to the normal blood plasma ratio set on the operation screen illustrated in FIG. 5. As a determination result, in a case where the required number of vacant specimen containers is not installed at a predetermined position, the preparation of the specimen is stopped, and a system alarm is displayed on the display unit 118c (Step S605). On the other hand, as a determination result, in a case where the vacant specimen container is installed at the predetermined position, the process proceeds to Step S606 so as to check the blood plasma amount by using the liquid level detection function of the specimen dispensing mechanism 101.

Incidentally, 3 points at the minimum are recommended for the number of measurements in the cross mixing test. In other words, the cross mixing test can be carried out if the number is 3 points or more. FIG. 21 illustrates a display example of the operation screen when the cross mixing test is requested according to the present embodiment. As illustrated in FIG. 21, the cross mixing test measurement request screen has a region in which the priorities of the normal blood plasma ratio can be selected. In the example illustrated in FIG. 21, the input can be made in three sequential stages from the highest priority. That is, the priority set in the priority setting region has a relationship of "priority 1>priority 2>priority 3". In addition, the example shows a state where the priority 1 is set when the normal blood plasma ratio is 0%, 50%, and 100%, the priority 2 is set when the normal blood plasma ratio is 10% and 20%, and the priority 3 is set when the normal blood plasma ratio is 80% and 90%. These set priorities are stored in the storage unit 119.

In addition, FIGS. 22 to 24 illustrate a relationship between the normal blood plasma amount and the subject blood plasma amount which correspond to the respective normal blood plasma ratios. As illustrated in FIG. 22, under the seven conditions of the normal blood plasma ratio of 0%, 10%, 20%, 50%, 80%, 90%, 100%, in a case where 200 µL of the mixed blood plasma is produced and the cross mixing test is carried out, each required amount of the normal blood plasma and the subject blood plasma is 700 µL or more. Here, a method for obtaining an effective analysis result will be described. The method uses a small amount of blood plasma even in a case where any one or both of these do not satisfy the required amount.

Here, referring back to FIG. 20, in Step S607, it is determined whether or not the normal blood plasma amount is equal to or more than $X_N$ and whether or not the subject blood plasma amount is equal to or more than $Y_N$. Here, $X_N$ is 700 µL in the example illustrated in FIG. 22, and $Y_N$ is similarly 700 µL. As a determination result, in a case where any one or both of "the normal blood plasma amount $X_N$" and "the subject blood plasma amount $Y_N$" do not satisfy the condition, that is, in a case where the blood plasma amount does not satisfy the required amount, the process proceeds to Step S608.

In Step S608, in order to change the number of measurement points, the priority set for each of the normal blood plasma ratios stored in the storage unit 119 is verified, and the condition corresponding to priority 3 is excluded, thereby recalculating the blood plasma amount. In Step S609, it is determined whether or not "the normal blood plasma amount$\geq(X_N-X_{P3})$" and "the subject blood plasma amount$\geq(Y_N-Y_{P3})$" are satisfied. Here, the normal blood plasma amount $(X_N-X_{P3})$ when the measurement is performed under the condition excluding the priority 3 is 360 µL, the subject blood plasma amount $(Y_N-Y_{P3})$ when the measurement is performed under the condition excluding the priority 3 is 640 µL (FIG. 23). As a determination result, in a case where any one or both of "the normal blood plasma amount$\geq(X_N-X_{P3})$" and "the subject blood plasma amount $(Y_N-Y_{P3})$" do not satisfy the condition, the process proceeds to Step S610. On the other hand, as a determination result, in a case where the above-described condition is satisfied, the process proceeds to Step S613.

In Step S610, the blood plasma amount at the time of measurement is recalculated under the condition that only the priority 1 is set, that is, under the condition that the conditions of priority 2 and priority 3 are excluded. Here, the normal blood plasma amount of 300 µL and the subject blood plasma amount of 300 µL are obtained as a recalculated blood plasma amount (FIG. 24). Next, the process proceeds to Step S611 so as to determine whether "the normal blood plasma amount$\geq(X_N-X_{P3}-X_{P2})$" and "the subject blood plasma amount to be examined $(Y_N-Y_{P3}-Y_{P2})$" are satisfied. As a determination result, in a case where any one or both of "the normal blood plasma amount $(X_N-X_{P3}-X_{P2})$" and "the subject blood plasma amount to be examined$\geq(Y_N-Y_{P3}-Y_{P2})$" do not satisfy the condition, the process proceeds to S612. A system alarm is output to the display unit 118c, and preparing the mixed blood plasma is stopped. On the other hand, as a determination result, in a case where the above-described condition is satisfied, the process proceeds to Step S613.

In Step S613, the analysis operation control unit 120a controls the specimen dispensing mechanism 101 and the reagent dispensing mechanism 106 so as to start dispensing the normal blood plasma and the subject blood plasma. Dispensing the normal blood plasma and the subject blood plasma is similar to that according to Example 1 described above, and thus, description thereof will be omitted here. If all of the normal blood plasma and the subject blood plasma are completely dispensed (Step S614), the analysis operation control unit 120a controls the stirring mechanism 126 so as to stir the mixed blood plasma (Step S615). After the mixed blood plasma is stirred, the analysis is performed.

In FIG. 20, a case where the priorities are set in three stages has been described as an example. However, without being limited thereto, the priorities can be optionally set.

According to the present embodiment, in addition to the advantageous effect of Example 1 and Example 2 described above, it is possible to obtain effective cross mixing measurement results, even in a case where the condition does not satisfy the normal blood plasma amount and/or the subject blood plasma amount which are for the measurement corresponding to the initially set normal blood plasma ratio.

The present invention is not limited to the above-described embodiments, and includes various modifications. For example, the above-described embodiments have been described in detail in order to facilitate the understanding of the present invention, and the present invention is not necessarily limited to those including all of the described configurations. In addition, a configuration of one embodiment can be partially substituted with a configuration of the other embodiment. Alternatively, the configuration of the other embodiment can be added to the configuration of one embodiment. Alternatively, additions, omissions, and substitutions of the configuration of the other embodiment can be made for a portion of the configuration in each embodiment.

REFERENCE SIGNS LIST

100: AUTOMATIC ANALYSIS DEVICE
101: SPECIMEN DISPENSING MECHANISM
101a: SPECIMEN DISPENSING PROBE
102: SPECIMEN DISC
103: SPECIMEN CONTAINER
104: REACTION CONTAINER
105: SPECIMEN SYRINGE PUMP
106: REAGENT DISPENSING MECHANISM
106a: REAGENT DISPENSING PROBE
107: REAGENT DISC
108: REAGENT CONTAINER
108a: REAGENT
109: REAGENT TEMPERATURE RAISING MECHANISM
110: REAGENT SYRINGE PUMP
111: REACTION CONTAINER STOCK UNIT
112: REACTION CONTAINER TRANSPORT MECHANISM
113: DETECTING UNIT
114: REACTION CONTAINER INSTALLATION UNIT
115: LIGHT SOURCE
116: DETECTOR (LIGHT RECEIVING UNIT)
117: REACTION CONTAINER DISPOSAL UNIT
118: OPERATION UNIT
118a: MOUSE
118b: KEYBOARD
118c: DISPLAY UNIT
119: STORAGE UNIT
120: CONTROL UNIT
120a: ANALYSIS OPERATION CONTROL UNIT
120b: CALCULATION UNIT
121: A/D CONVERTER
122: INTERFACE
123: PRINTER
124: INCUBATOR
125: READING UNIT
126: STIRRING MECHANISM
127: TEST ITEM SELECTION/DESIGNATION REGION
201: SPECIMEN RACK
202: SPECIMEN RACK SUPPLY UNIT
203: SPECIMEN RACK ACCOMMODATION UNIT
204: TRANSPORT LINE
205: RETURN LINE
206: SPECIMEN RACK STANDBY UNIT
207: STANDBY UNIT HANDLING MECHANISM
208: RACK RETURNING MECHANISM
209: FIRST READING UNIT (TRANSPORT LINE)
210: ANALYSIS UNIT
211: SECOND READING UNIT (ANALYSIS UNIT)
212: FIRST RACK HANDLING MECHANISM
213: DISPENSING LINE
214: EVACUATION AREA
215: SECOND RACK HANDLING MECHANISM

The invention claimed is:
1. An automatic analysis device comprising:
a specimen container holding unit that accommodates and holds a plurality of specimen containers;
a specimen dispensing mechanism that dispenses only subject blood plasma, dispenses only normal blood plasma, and dispenses both the subject blood plasma and the normal blood plasma at a first predetermined mixing ratio of the subject blood plasma and the normal blood plasma to a plurality of vacant specimen containers, respectively;
a plurality of reaction containers to which the specimen dispensing mechanism respectively dispenses the subject blood plasma alone, the normal blood plasma alone, and both the subject blood plasma and the normal blood plasma at the first predetermined mixing ratio after they are prepared in the plurality of vacant specimen containers, respectively;
a reagent dispensing mechanism that dispenses a reagent to each of the plurality of reaction containers;
a measurement unit that irradiates each of the plurality of reaction containers with light emitted from a light source, and that measures a plurality of coagulation times, respectively, based on obtained scattered light and/or transmitted light; and
a control unit configured to control the specimen dispensing mechanism to perform an immediate-type measurement by dispensing the subject blood plasma alone, the normal blood plasma alone, and both the subject blood plasma and the normal blood plasma at the first predetermined mixing ratio immediately after they are prepared in the plurality of vacant specimen containers into the plurality of reaction containers, respectively, to measure immediate-type coagulation times, and configured to control the specimen dispensing mechanism to automatically perform a delayed-type measurement by dispensing the subject blood plasma alone, the normal blood plasma alone, and both the subject blood plasma and the normal blood plasma at the first predetermined mixing ratio into another plurality of reaction containers, respectively, after a predetermined time elapses to measure delayed-type coagulation times.
2. The automatic analysis device according to claim 1, wherein the control unit that controls the specimen dispensing mechanism to perform the immediate-type measurement and the delayed-type measurement for at least one mixture of both the subject blood plasma and the normal blood plasma at least at one other predetermined mixing ratio different from the first predetermined mixing ratio.
3. The automatic analysis device according to claim 1, wherein the specimen container holding unit is a specimen rack that contains the subject blood plasma alone, the normal blood plasma alone, and both the subject blood plasma and the normal blood plasma at the first predetermined mixing ratio,
wherein the automatic analysis device further comprises a specimen rack supply unit that accommodates a plurality of the specimen racks;

a transport line that transports the specimen rack from the specimen rack supply unit to the measurement unit; and a return line that transports the specimen rack from the measurement unit to a specimen rack accommodation unit.

4. The automatic analysis device according to claim 1, further comprising:

a display unit that graphically displays the plurality of coagulation times for the immediate-type measurement and the delayed-type measurement.

5. The automatic analysis device according to claim 1, further comprising:

an incubator that warms the reaction containers containing the subject blood plasma alone, the normal blood plasma alone and both the subject blood plasma and the normal blood plasma at the first predetermined mixing ratio at a predetermined temperature for a predetermined amount of time.

6. The automatic analysis device according to claim 5, wherein the reagent dispensing mechanism dispenses the reagent to the reaction containers containing the subject blood plasma alone, the normal blood plasma alone and both the subject blood plasma and the normal blood plasma at the first predetermined mixing ratio which are warmed for the predetermined amount time, and the measurement unit measures the coagulation time.

7. The automatic analysis device according to claim 4, wherein information of the subject blood plasma alone, the normal blood plasma alone and both the subject blood plasma and the normal blood plasma at the first predetermined mixing ratio is managed by using individual identification media.

8. The automatic analysis device according to claim 2, further comprising:

a liquid level detecting mechanism that confirms an amount of the subject blood plasma, an amount of the normal blood plasma, and a presence of the plurality of vacant specimen containers in advance.

9. The automatic analysis device according to claim 8, wherein priorities are set in advance for the subject blood plasma alone, the normal blood plasma alone, and the both the subject blood plasma and the normal blood plasma at the first predetermined mixing ratio, and wherein in a case where a shortage of the amount of the subject blood plasma and/or the amount of the normal blood plasma is predicted, in order to measure the coagulation times, based on the set priorities, a combination is determined among the first predetermined mixing ratio and the at least one other predetermined mixing ratio.

10. The automatic analysis device according to claim 2, wherein a remaining amount of the reagent is managed for each reagent container, and a reagent container to be used is controlled in accordance with a number of reaction containers to be used.

11. The automatic analysis device according to claim 1, wherein the measurement unit gives a priority to and measures a specimen according to the priority.

12. The automatic analysis device according to claim 11, further comprising:

an operation unit that presets priorities for an urgent specimen, a general specimen, and a specimen containing both the subject blood plasma and the normal blood plasma at the first predetermined mixing ratio for measuring the coagulation times.

13. The automatic analysis device according to claim 9, further comprising:

a storage unit that stores each of the priorities; and a control unit that performs control so that the specimen corresponding to the priority stored in the storage unit is transported to the measurement unit via a specimen disc or a transport line.

14. The automatic analysis device according to claim 1, wherein the specimen container holding unit is a specimen disc that causes the subject blood plasma, the normal blood plasma, and both the subject blood plasma and the normal blood plasma at the first predetermined mixing ratio to be contained in the vacant specimen containers which are annularly arrayed separately from each other.

15. An automatic analysis method of an automatic analysis device which has at least a specimen container holding unit that accommodates and holds a plurality of specimen containers, a specimen dispensing mechanism, a reagent dispensing mechanism, a measurement unit, and a control unit, the method comprising:

dispensing, by the specimen dispensing mechanism, only subject blood plasma, only normal blood plasma, and both the subject blood plasma and the normal blood plasma at a first predetermined mixing ratio of the subject blood plasma and the normal blood plasma to a plurality of vacant specimen containers, respectively, accommodated in the specimen container holding unit;

dispensing the subject blood plasma alone, the normal blood plasma alone, and both the subject blood plasma and the normal blood plasma at the first predetermined mixing ratio after they are prepared in the plurality of vacant specimen containers to a plurality of reaction containers, respectively;

dispensing, by the reagent dispensing mechanism, a reagent to each of the plurality of reaction containers;

irradiating each of the plurality of reaction containers with light emitted from a light source, and measuring a plurality of coagulation times, respectively, based on obtained scattered light and/or transmitted light; and controlling the specimen dispensing mechanism to perform an immediate-type measurement by dispensing the subject blood plasma alone, the normal blood plasma alone, and both the subject blood plasma and the normal blood plasma at the first predetermined mixing ratio immediately after they are prepared in the plurality of vacant specimen containers into the plurality of reaction containers, respectively, to measure immediate-type coagulation times, and that controlling the specimen dispensing mechanism to automatically perform a delayed-type measurement by dispensing the subject blood plasma alone, the normal blood plasma alone, and both the subject blood plasma and the normal blood plasma at the first predetermined mixing ratio into another plurality of reaction containers, respectively, after a predetermined time elapses to measure delayed-type coagulation times.

16. The automatic analysis method according to claim 15, further comprising:

causing a display unit to graphically display the plurality of coagulation times for the immediate-type measurement and the delayed-type measurement.

17. The automatic analysis method according to claim 15, further comprising:

warming the reaction containers containing the subject blood plasma alone, the normal blood plasma alone and both the subject blood plasma and the normal blood plasma at the first predetermined mixing ratio at a predetermined temperature for a predetermined amount of time; and dispensing the reagent to the reaction containers after being warmed for the predetermined amount of time, and measuring the coagulation times.

18. The automatic analysis method according to claim 15, further comprising:

presetting priorities for the subject blood plasma alone, the normal blood plasma alone, and both the subject blood plasma and the normal blood plasma at the first predetermined mixing ratio and at least one mixture of both the subject blood plasma and the normal blood plasma at least at one other predetermined mixing ratio different from the first predetermined mixing ratio; and determining a combination among the first predetermined mixing ratio and the at least one other predetermined mixing ratio in order to measure the coagulation times, based on the set priorities.

19. The automatic analysis method according to claim 15, further comprising:

presetting priorities for an urgent specimen, a general specimen, and a specimen containing both the subject blood plasma and the normal blood plasma at the first predetermined mixing ratio for measuring the coagulation time; and changing an analysis order in accordance with the set priorities.

20. An automatic analysis device comprising:

a specimen container holding unit that accommodates and holds a plurality of specimen containers;

a specimen dispensing mechanism that dispenses only subject blood plasma, dispenses only normal blood plasma, and dispenses both subject blood plasma and normal blood plasma at a first predetermined mixing ratio of the subject blood plasma and the normal blood plasma to a plurality of vacant specimen containers, respectively;

a reagent dispensing mechanism that dispenses a reagent to each of a plurality of reaction containers to which the specimen dispensing mechanism respectively dispenses the subject blood plasma alone, the normal blood plasma alone, and both the subject blood plasma and the normal blood plasma at the first predetermined mixing ratio after they are prepared in the plurality of vacant specimen containers, respectively;

a measurement unit that irradiates each of the plurality of reaction containers with light emitted from a light source, and that measures a plurality of coagulation times, respectively, based on obtained scattered light and/or transmitted light; and a control unit configured to control the specimen dispensing mechanism to perform an immediate-type measurement by dispensing the subject blood plasma alone, the normal blood plasma alone, and both the subject blood plasma and the normal blood plasma at the first predetermined mixing ratio immediately after they are prepared in the plurality of vacant specimen containers into the plurality of reaction containers, respectively, to measure immediate-type coagulation times, and configured to control the specimen dispensing mechanism to automatically perform a delayed-type measurement by dispensing the subject blood plasma alone, the normal blood plasma alone, and both the subject blood plasma and the normal blood plasma at the first predetermined mixing ratio into another plurality of reaction containers, respectively, after a predetermined time elapses to measure delayed-type coagulation times.

* * * * *